(12) United States Patent
Dexter et al.

(10) Patent No.: US 8,459,414 B2
(45) Date of Patent: *Jun. 11, 2013

(54) LUBRICATION AND EXHAUST SYSTEM FOR A POWERED SURGICAL INSTRUMENT

(71) Applicant: Medtronic Xomed, Inc., Jacksonville, FL (US)

(72) Inventors: S. Shane Dexter, Fort Worth, TX (US); Larry D. Estes, North Richland Hills, TX (US); Gabriel A. Johnston, Raynham, MA (US); Durrell G. Tidwell, Burleson, TX (US); Bret Hauser, Flower Mound, TX (US); Lauren Devita, Fort Worth, TX (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,157

(22) Filed: Oct. 8, 2012

(65) Prior Publication Data

US 2013/0032435 A1 Feb. 7, 2013

Related U.S. Application Data

(63) Continuation of application No. 12/483,046, filed on Jun. 11, 2009, now Pat. No. 8,281,898.

(51) Int. Cl.
*F16N 27/00* (2006.01)

(52) U.S. Cl.
USPC ........................................................ 184/7.4

(58) Field of Classification Search
USPC ................. 184/7.4, 6.24, 55.1, 55.2; 604/12, 604/172, 265; 606/107, 159
See application file for complete search history.

(56) References Cited

U.S. PATENT DOCUMENTS

| | | |
|---|---|---|
| 2,792,073 A | 5/1957 | Boss |
| 2,878,895 A | 3/1959 | Wiley |
| 4,218,216 A | 8/1980 | Sugai et al. |
| 4,310,309 A | 1/1982 | Favonio |
| 4,721,186 A | 1/1988 | Fujiwara |
| 5,328,657 A | 7/1994 | Kamel et al. |
| 5,427,203 A | 6/1995 | Anspach, Jr. et al. |

(Continued)

FOREIGN PATENT DOCUMENTS

| | | |
|---|---|---|
| AU | 2010258919 A1 | 12/2011 |
| CA | 2764388 A1 | 12/2010 |

(Continued)

OTHER PUBLICATIONS

Manufacturingtalk; "Growing use of porous metal in medical devices"; 2008; pp. 1-2; Pro-Talk Ltd.; UK; http://www.manufacturingtalk.com/news/mtc./mtc118.html.

(Continued)

*Primary Examiner* — Michael Mansen
*Assistant Examiner* — Robert T Reese
(74) *Attorney, Agent, or Firm* — Harness, Dickey

(57) ABSTRACT

A lubrication cartridge includes a cartridge body. A cartridge coupling is located on the cartridge body and defines a first passage and a second passage. A lubricant reservoir is housed in the cartridge body and comprises a pressurized fluid inlet coupled to the first passage and a lubricant outlet coupled to the second passage. A metering insert is located between the lubricant outlet and the second passage and comprises a density that controls lubricant flow between the lubricant reservoir and the second passage.

27 Claims, 21 Drawing Sheets

U.S. PATENT DOCUMENTS

| | | |
|---|---|---|
| 6,152,162 A | 11/2000 | Balazy et al. |
| 6,283,141 B1 | 9/2001 | Saxback et al. |
| 6,457,236 B1 | 10/2002 | White et al. |
| 6,920,960 B2 | 7/2005 | Highley |
| 7,008,224 B1 | 3/2006 | Browning et al. |
| 8,281,898 B2 | 10/2012 | Dexter et al. |
| 2003/0000774 A1 | 1/2003 | Highley |
| 2005/0189178 A1 | 9/2005 | Highley |

FOREIGN PATENT DOCUMENTS

| | | |
|---|---|---|
| EP | 0853925 A1 | 7/1998 |
| EP | 2440831 A1 | 4/2012 |
| FR | 2447460 A1 | 8/1980 |
| GB | 1204607 A | 9/1970 |
| JP | 2012529354 A | 11/2012 |
| WO | WO-2010144440 A1 | 12/2010 |

OTHER PUBLICATIONS

Medtronic Midas Rex; "Medtronic Midas Rex Instrumentation System"; Instruction Manual; 2000; pp. 1-24; Medtronic Midas Rex; France.

International Search Report mailed Sep. 17, 2010 for PCT/US2010/037760 claiming benefit of U.S. Appl. No. 12/483,046, filed Jun. 11, 2009.

International Preliminary Report and Written Opinion mailed Dec. 12, 2011 for PCT/US2010/037760 claiming benefit of U.S. Appl. No. 12/483,046, filed Jun. 11, 2009.

LUBRICATION AND EXHAUST SYSTEM FOR A POWERED SURGICAL INSTRUMENT

CROSS REFERENCE TO RELATED APPLICATIONS

This application is a continuation of U.S. application Ser. No. 12/483,046 filed on Jun. 11, 2009. The disclosure of the above application is incorporated herein by reference.

FIELD

The present invention generally relates to surgical instruments. More particularly, the present invention relates to a lubrication and exhaust system for use with powered surgical instruments.

BACKGROUND

Doctors and other medical professionals often use powered surgical instruments for dissecting bones and tissues, and for a variety of other purposes. Frequently, it is important to lubricate the instruments for proper usages. For example, a pneumatically powered surgical instrument may include a pneumatic motor that is connected to a fluid supply source, and a lubrication system is typically placed inline between the fluid supply source and the pneumatic motor to provide lubrication to the surgical instrument.

Traditionally, the lubrication system must be manually calibrated and/or activated according to predetermined guidelines. For example, the lubrication system may be set at a specific dripping rate for providing oil to the surgical instrument. Therefore, to supply a certain amount of lubrication to the instrument, it is important to maintain a proper dripping rate. However, such manual operation is prone to mistakes and inaccuracy, and the amount of supplied oil may vary such that too much or too little oil may be provided to the surgical instrument. This can result in premature wear of the surgical instrument in the case of too little oil, and possible leaking and contamination of an operating room in the case of too much oil.

Therefore, it is desired to provide an improved lubrication system.

SUMMARY

The present invention provides an improved lubrication system for a surgical instrument.

In one embodiment, a lubrication cartridge includes a cartridge body, a cartridge coupling located on the cartridge body and defining a first passage and a second passage, a lubricant reservoir housed in the cartridge body and comprising a pressurized fluid inlet coupled to the first passage and a lubricant outlet coupled to the second passage, and a metering insert located between the lubricant outlet and the second passage and comprising a density that controls lubricant flow between the lubricant reservoir and the second passage.

In another embodiment, a surgical instrument lubrication system includes a lubrication cartridge, a stem defining a primary fluid path, a quarter-turn coupling interface located on each of the lubrication cartridge stem that is operable to sealing mate the lubrication cartridge with the stem, wherein the lubrication cartridge and the stem comprising an initial coupling orientation and a final coupling orientation, and wherein the lubrication cartridge is rotated approximately 90 degrees relative to the stem between the initial coupling orientation and the final coupling orientation, a lubricant reservoir housed in the lubrication cartridge, a metering insert located between the lubricant reservoir and the primary fluid path and operable to meter lubricant flow from the lubricant reservoir to the primary flow path, and an exhaust portion housed in the lubrication cartridge and operable to filter exhaust fluid that passes through the lubrication cartridge.

In yet another embodiment, a surgical system includes a surgical instrument, a fluid supply system operable to supply a pressurized fluid to the surgical instrument to power the surgical instrument, a stem comprising: a quarter-turn stem coupling, a pressurized fluid entry port in fluid communication with a pressurized fluid exit port via a primary fluid path, wherein the pressurized fluid entry port is coupled to the fluid supply system and the pressurized fluid exit port is coupled to a tubing that is further coupled to the surgical instrument and operable to transmit pressurized fluid from the stem to the surgical instrument and transmit exhaust fluid from the surgical instrument to the stem, a Venturi neck located along the primary fluid path, a high pressure tap in fluid communication with the primary fluid path upstream from the Venturi neck; and a suction tap in fluid communication with the Venturi neck, a lubrication cartridge comprising: a quarter-turn lubrication coupling mateable with the quarter-turn stem coupling, a high pressure area annulus defined by the quarter-turn lubrication coupling, and a passage defined by the quarter-turn lubrication coupling and including an passage entrance located within the high pressure area annulus, a lubricant reservoir in fluid communication with the high pressure tap through the high pressure area annulus, a first delivery tube extending into the lubricant reservoir, a metering insert located between the suction tap and the first delivery tube, an exhaust passage operable to receive exhaust fluid transmitted from the from the surgical instrument, through the tubing, and to the stem; and an exhaust filter operable to remove lubricant located in the exhaust fluid.

It should be understood that the present summary and the following detailed description, while indicating embodiments of the invention, are intended for purposes of illustration only and are not intended to limit the scope of the invention beyond that described in the claims.

BRIEF DESCRIPTION OF THE DRAWINGS

The present disclosure will become more fully understood from the detailed description and the accompanying drawings, wherein:

FIG. 2b is a top view illustrating an embodiment of the lubrication system of FIG. 2a.

FIG. 4b is a perspective view illustrating an embodiment of a cartridge coupling on the lubrication cartridge of FIG. 4a.

FIG. 4c is a cut-away perspective view illustrating an embodiment of a cartridge coupling on the lubrication cartridge of FIG. 4a.

FIG. 4d is an exploded view illustrating an embodiment of the lubrication cartridge of FIG. 4a.

FIG. 5b is a perspective view illustrating an embodiment of the stem of FIGS. 5a.

DETAILED DESCRIPTION

Figure 1A:
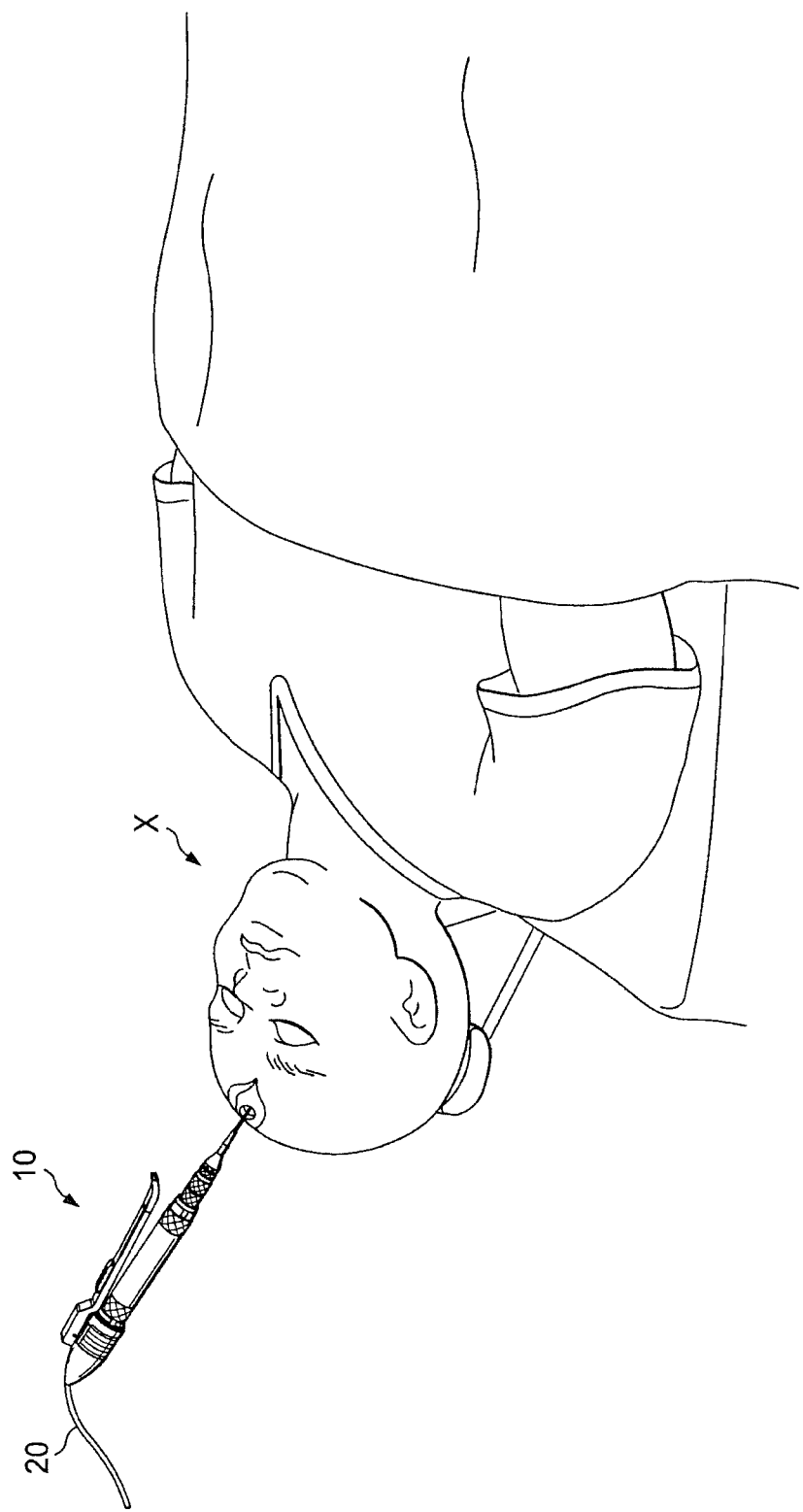
FIG. 1a is a perspective view illustrating an embodiment of a surgical instrument being used on a patient.

For the purposes of promoting an understanding of the principles of the disclosure, references will now be made to the embodiments, or examples, illustrated in the drawings and specific languages will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one skilled in the art to which the disclosure relates.

Figure 1B:
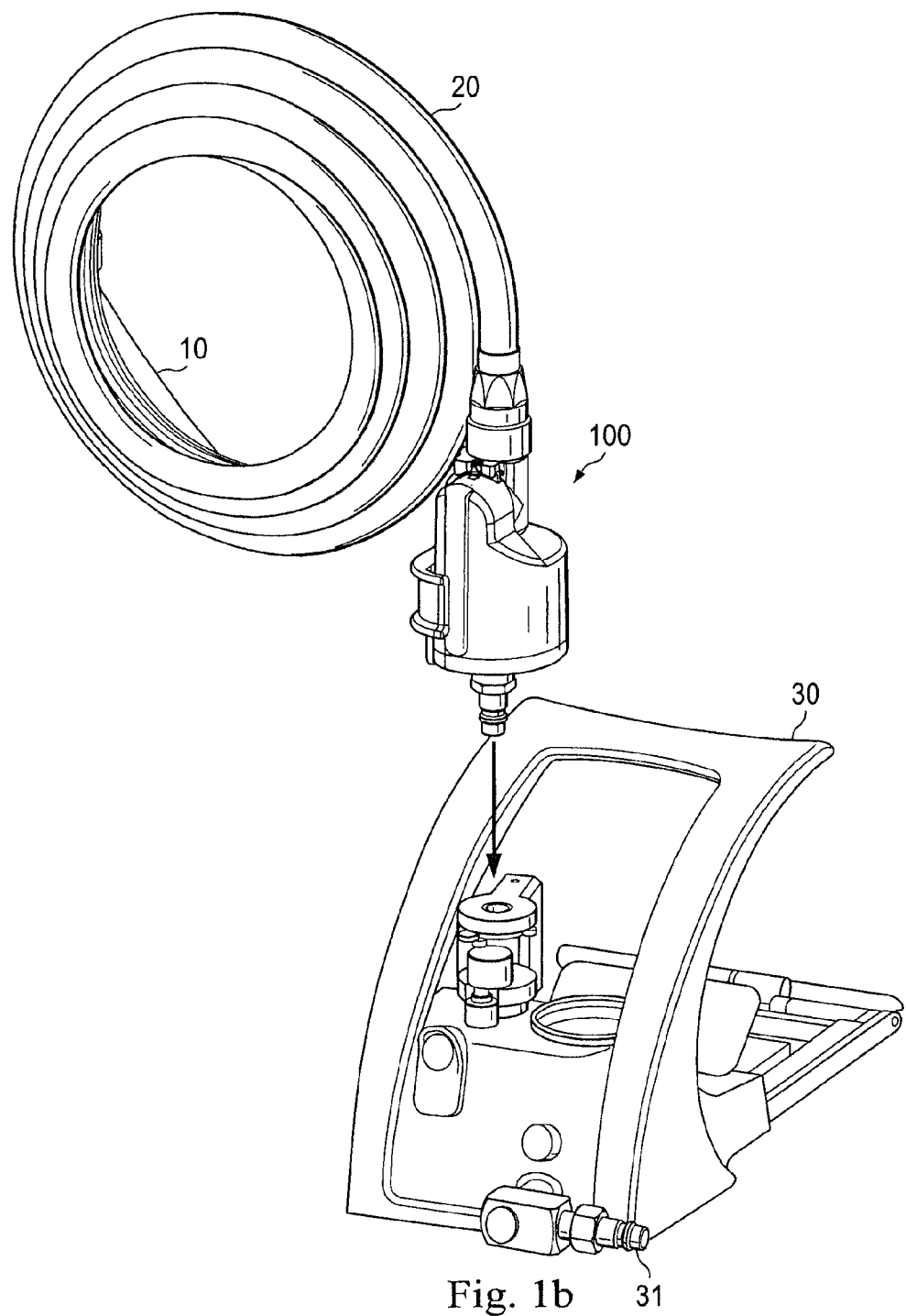
FIG. 1b is a perspective view illustrating an embodiment of the surgical instrument of FIG. 1a coupled to a lubrication system that may be further coupled to a pneumatic supply system.

Referring initially to FIG. 1a, a surgical instrument for the dissection of bone and other tissue is illustrated and generally identified at reference numeral 10. The embodiment of the surgical instrument 10 illustrated in FIG. 1 is operatively associated with a patient X for performing a craniotomy. However, it will become apparent to those skilled in the art that the subject invention is not limited to any particular surgical application but has utility for various applications in which it is desired, including but not limited to:

1. Arthroscopy—Orthopedic
2. Endoscopic—Gastroenterology, Urology, Soft Tissue
3. Neurosurgery—Cranial, Spine, and Otology
4. Small Bone—Orthopedic, Oral-Maxiofacial, Ortho-Spine, and Otology
5. Cardio Thoracic—Small Bone Sub-Segment
6. Large Bone—Total Joint and Trauma
7. Dental and other applications Referring now to FIGS. 1a and 1b, the surgical instrument 10 is coupled to a tubing 20, and the tubing 20 is coupled to a lubrication system 100. In an embodiment, the lubrication system 100 may be directly coupled to a foot pedal switch 30 that includes a coupling 31 that may be coupled to pneumatic supply system such that a fluid (e.g., air) may be provided from the pneumatic supply system, through the foot pedal switch 30, the lubrication system 100, and the tubing 20, and then to the surgical instrument 10. In an embodiment, the lubrication system 100 may be coupled directly to the pneumatic supply system.

Referring now to FIGS. 2a, 2b, 2c, 2d, and 2e, an exemplary embodiment of the lubrication system 100 is illustrated. The lubrication system 100 includes a lubrication cartridge 102 coupled to a stem 104. As described above with reference to FIGS. 1a and 1b, the lubrication system 100 may be used inline between a pneumatic supply system and a pneumatically powered surgical instrument (e.g., the surgical instrument 10) to provide metered lubrication to the surgical instrument 10. Exemplary surgical instruments are disclosed in U.S. Pat. Nos. 5,505,737 and 7,011,661, which are commonly owned and hereby incorporated by reference in their entirety as if fully set forth herein. However, it is contemplated that the teachings of the present disclosure also apply to other powered instruments and fluid powered devices.

Figure 2A:
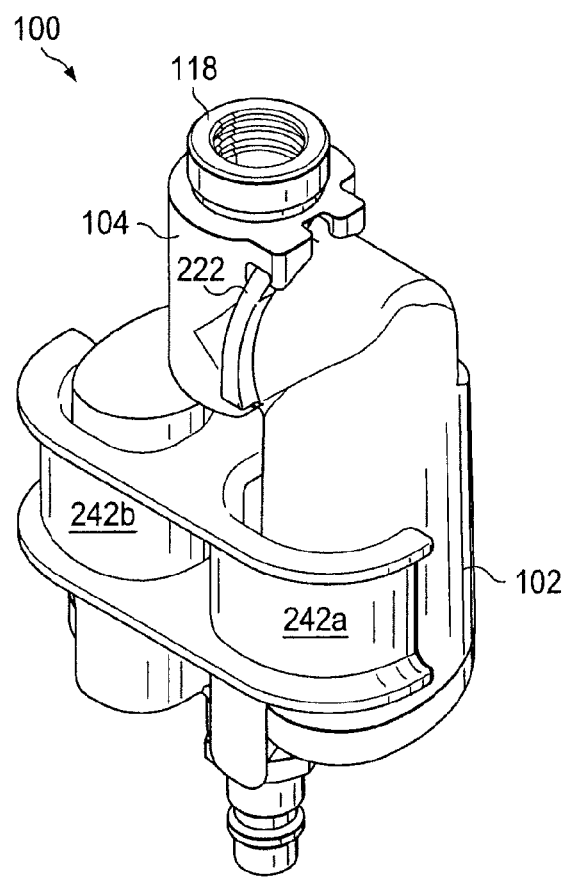
FIG. 2a is a perspective view illustrating an embodiment of the lubrication system of FIG. 1b.
Figure 2B:
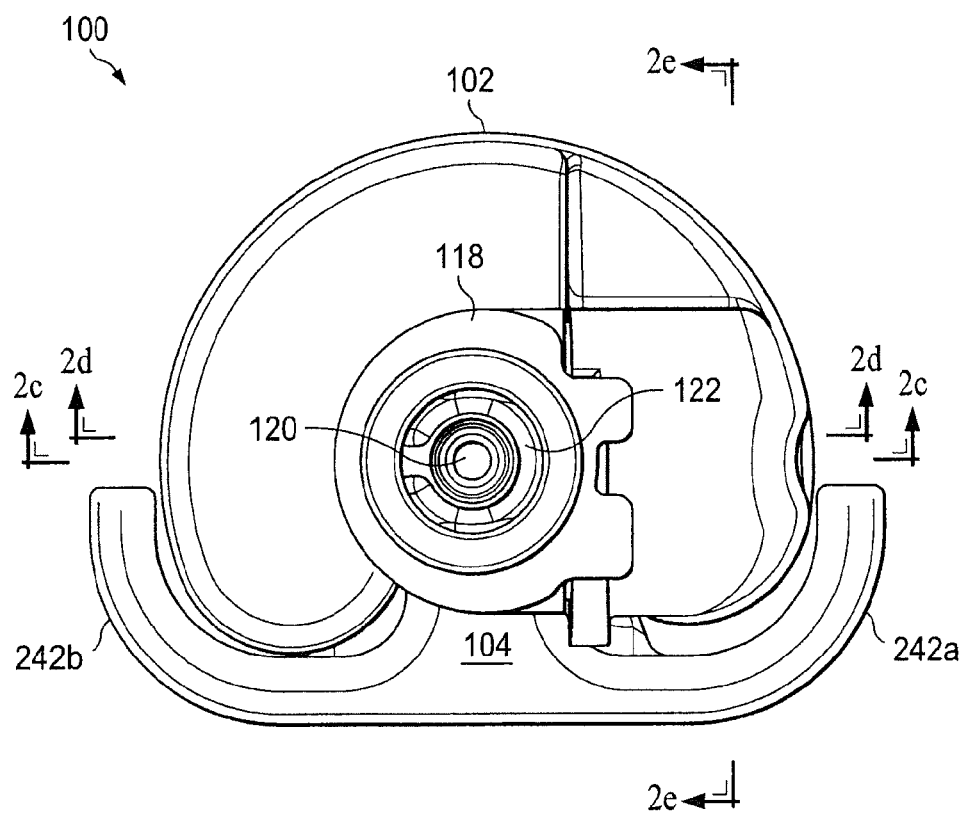

FIG. 2b illustrates a top view of the lubrication system 100 of FIG. 2a. A plurality of internal passages and volumes included within the lubrication cartridge 102 and the stem 104 will be described below with reference to the various cross-section views illustrated in FIG. 2b.

Figure 2C:
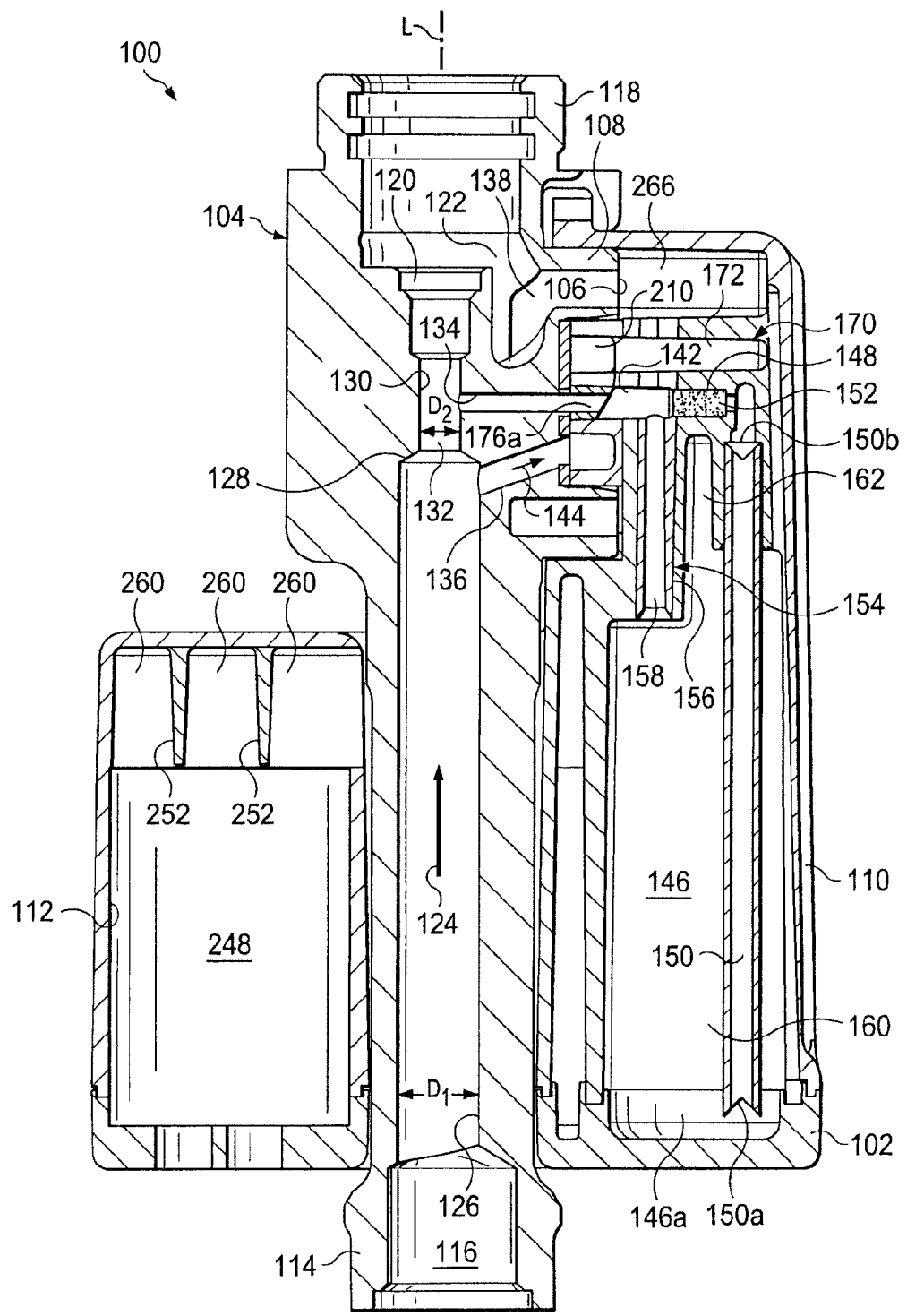
FIG. 2c is a cross-sectional view of the lubrication system of FIGS. 2a and 2b taken along line 2c-2c of FIG. 2b.

FIG. 2c illustrates a longitudinal cross-sectional view of the lubrication system 100 taken along line 2c-2c in FIG. 2b. The lubrication cartridge 102 may generally be a closed body or housing with a multi-ported cartridge coupling 106 (also illustrated in FIGS. 2d, 4a, 4b, 4c, 4d, and 6a) which couples to a multi-ported stem coupling 108 (also illustrated in FIGS. 2d, 5a, and 6a) on the stem 104. The lubrication cartridge 102 includes a lubrication portion 110 and an exhaust portion 112 which are both in fluid communication with the cartridge coupling 106.

In operation, pressurized fluid enters the lubrication system 100 through the stem 104. The stem 104 may generally includes an elongate stem or pipe that may be removably coupled inline between a pneumatic supply system and a pneumatically powered surgical instrument (e.g., the surgical instrument 10, as described above with reference to FIGS. 1a and 1b). The stem coupling 108 is in fluid communication with the lubrication portion 110 and the exhaust portion 112 of the lubrication cartridge 102 through a plurality of passages described below.

An upstream end of the stem 104 includes a coupling 114 with a central bore 116. A downstream end of stem 104 comprises a coupling 118 that includes a face that is substantially parallel but offset with the coupling 114. In an embodiment, the couplings 114 and 118 may be coaxial. As illustrated in FIGS. 2b and 2c, the coupling 118 generally comprises a central bore 120 for supplying high pressure fluid through the tubing 20 to the surgical instrument 10 and a coaxial outer bore 122 for receiving exhaust fluid returning from the surgical instrument 10 through the tubing 20. In other embodiments, a downstream coupling may include non-coaxial high pressure fluid and exhaust fluid bores.

As illustrated in FIG. 2c, the stem 104 includes a primary fluid path 124 that extends generally along a longitudinal axis L between the central bores 116 and 120 of the couplings 114 and 118. The primary fluid path 124 generally has a consistent first inner diameter $D_1$ and is defined by a first side wall 126. The primary fluid path 124 may include a Venturi section 128 that includes a neck 130 that is defined by a second side wall 132 and includes a second inner diameter $D_2$ that is smaller than diameter $D_1$. The second side wall 132 defines an entrance to a suction tap 134 that extends generally transverse to the primary fluid path 124. Upstream from the Venturi section 128, the first side wall 126 defines an entrance to a high pressure tap 136 that extends away from the primary fluid path 124 at an angle towards the stem coupling 108. At the downstream end of the stem 104, an exhaust passage 138 is in fluid communication with the coaxial outer bore 122 of the coupling 118.

Accordingly, the high pressure tap 136, the suction tap 134, and the exhaust passage 138 all open into the stem coupling 108 (when not isolated from the stem coupling 108 by a gasket system, described in further detail below). When the lubrication cartridge 102 is coupled to the stem 104, as described in further detail below, the stem coupling 108 is sealingly mated to the cartridge coupling 106, resulting in the high pressure tap 136 and the suction tap 134 being in fluid communication with the lubrication portion 110 of the lubrication cartridge 102, and the exhaust passage 138 being in fluid communication with the exhaust portion 112 of the lubrication cartridge 102.

Figure 2D:
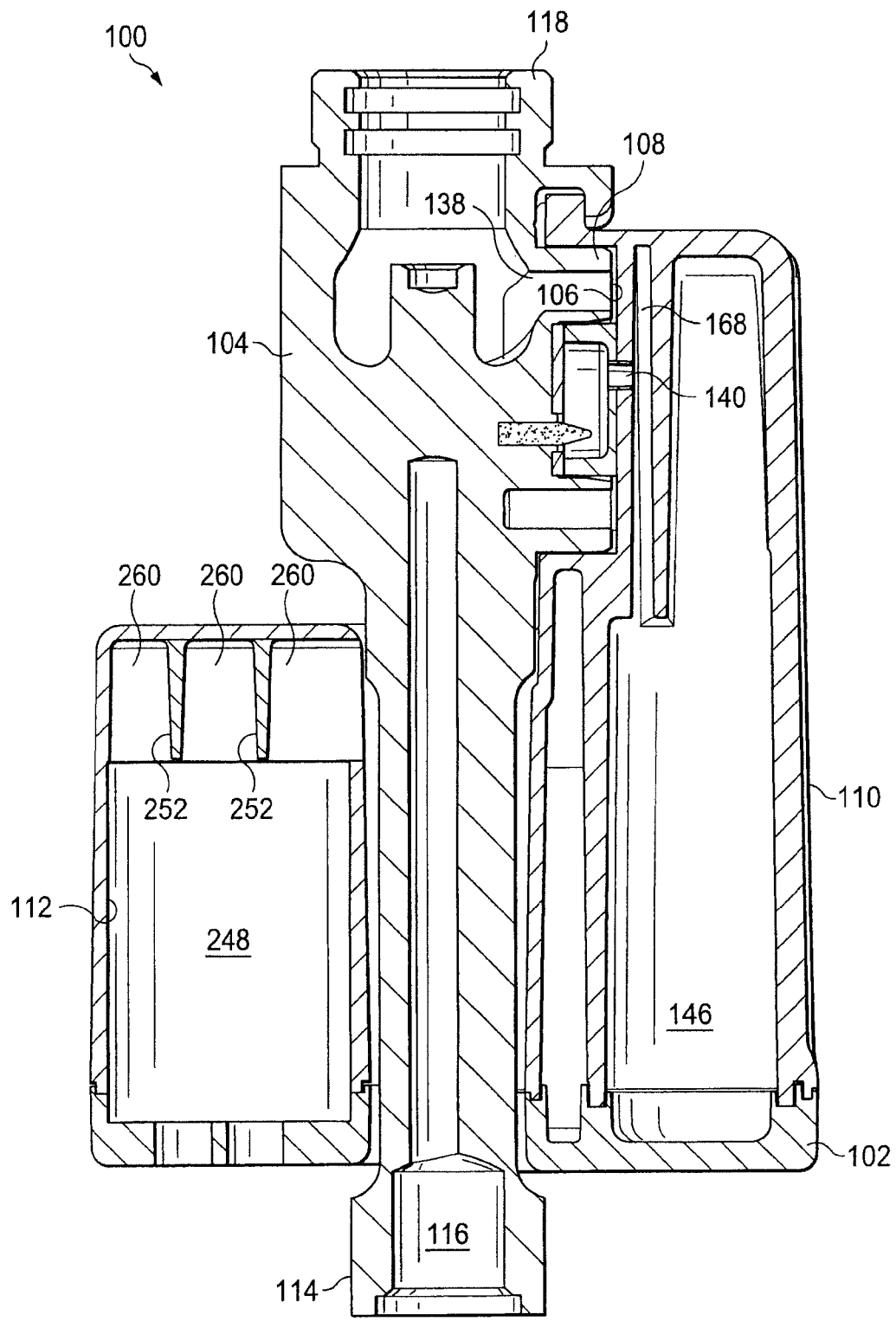
FIG. 2d is a cross-sectional view of the lubrication system of FIGS. 2a and 2b taken along line 2d-2d of FIG. 2b.

Referring now to FIGS. 2c and 2d, the lubrication cartridge 102 will be described in further detail. FIG. 2d illustrates a longitudinal cross-sectional view of the lubrication system 100 taken along line 2d-2d in FIG. 2b. The lubrication portion 110 includes a first passage 140 which is in sealed fluid communication with the high pressure tap 136 when the cartridge coupling 106 and the stem coupling 108 are mated. The lubrication portion 110 includes a second passage 142 which is in sealed fluid communication with the suction tap 134 when the cartridge coupling 106 and the stem coupling 108 are mated.

In operation, as a volume of pressurized fluid is introduced to the stem 104 through the central bore 116 of the coupling 114, it will travel directly through the stem 104 along the primary fluid path 124. A portion of that volume of pressurized fluid will be diverted along a secondary fluid path 144 through the high pressure tap 136 and into the first passage 140. The first passage 140 is in fluid communication with a lubricant reservoir 146 that is defined by the lubrication portion 110 of the lubrication cartridge 110. The second passage 142 is also in fluid communication with the lubricant reservoir 146, preferably through a metering portion 148. In operation, the Venturi section 128, high pressure tap 136, and the suction tap 134 create a fluid pressure differential that pulls lubricant from the lubricant reservoir 146 for deposit into the primary fluid path 124.

The lubricant reservoir 146 may include a small container or containment area 147 (illustrated in FIG. 6a) for a lubricant such as, for example, oil or other suitable lubricants known in the art. A first lubricant delivery tube 150 extends down into the lubricant reservoir 146 and may include a lower end 150a that is located near a bottom 146a of the lubricant reservoir 146. An upper end 150b of the lubricant delivery tube 150 is in fluid communication with the second passage 142 through the metering portion 148. In an embodiment, the lubricant reservoir 146 may contain a lubricant only. However, in other embodiments, the lubricant reservoir 146 may contain a porous media which is saturated with a lubricant. In addition, the lubricant reservoir 146 may include other features that will be described below.

The metering portion 148 preferably includes a porous metering insert 152 which, in operation, limits fluid flow and adds to the pressure differential across the Venturi section 128. The metering insert 152 may provide a plurality of fluid flow paths through pores defined by the metering insert. In an embodiment, the metering insert 152 is fabricated from a sintered metal powder and includes a plurality of flow paths which are randomly created by the adjoining of open pore spaces during sintering. By including the plurality of flow paths in the metering insert, if a particular pore space along a flow path through which lubricant is traveling becomes blocked during usage, the lubricant may pass through other, alternate flow paths. Thus, a porous metering insert, such as metering insert 152, includes numerous flow paths that provide redundancy against blockage of lubricant flow through the lubrication system 100.

In operation, the pressure differential created by the Venturi section 128, the high pressure tap 136, and the suction tap 134 pulls lubricant from the lubricant reservoir 146 through the first delivery tube 150 and through the metering insert 152 at a predictable and repeatable rate. The lubricant may exit the metering insert 152 as small lubricant droplets that may be atomized into the volume of pressurized fluid that was diverted along the secondary fluid path 144 through the high pressure tap 136 and into the first passage 140, and that diverted volume of pressurized air that includes the lubricant may then re-enter the primary fluid path 124 through the suction tap 134. The pressurized air that includes the lubricant may then travel through the stem 104 and the tubing 20 such that it is supplied to the surgical instrument 10. Thus, the metering insert 152 may provide metered delivery of lubricant to the surgical instrument 10 during operation.

In addition to sintering, the metering insert 152 may be fabricated from a variety of processes such as, for example, natural processes that are capable of producing a porous insert. In other embodiments, the fabrication of a porous metering insert yields a metering insert with a plurality of flow paths that are created from pores that are not randomly distributed. In an embodiment, the metering insert 152 may include a variety of materials such as, for example, ceramics, plastics, nano-materials, pumice, and/or a variety of other suitable materials known in the art.

Figure 3A:
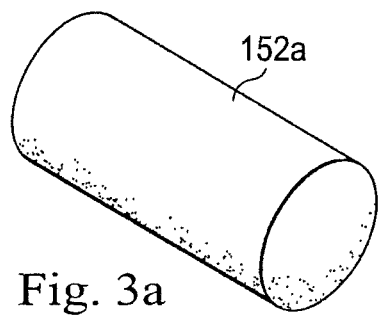
FIG. 3a is a perspective view illustrating an embodiment of a metering insert used with the lubrication system of FIGS. 2a, 2b, 2c, 2d, and 2e.
Figure 3B:
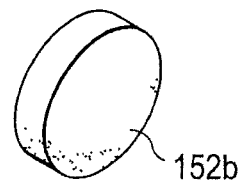
FIG. 3b is a perspective view illustrating an embodiment of a metering insert used with the lubrication system of FIGS. 2a, 2b, 2c, 2d, and 2e.
Figure 3C:
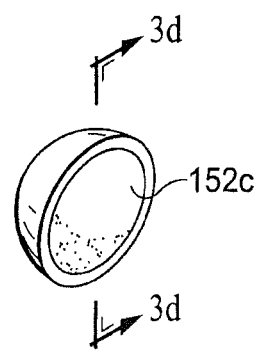
FIG. 3c is a perspective view illustrating an embodiment of a metering insert used with the lubrication system of FIGS. 2a, 2b, 2c, 2d, and 2e.
Figure 3D:
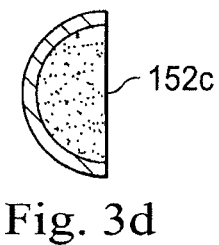
FIG. 3d is a cross-sectional view illustrating an embodiment of metering insert of FIG. 3c taken along line 3d-3d in FIG. 3c.
Figure 3E:
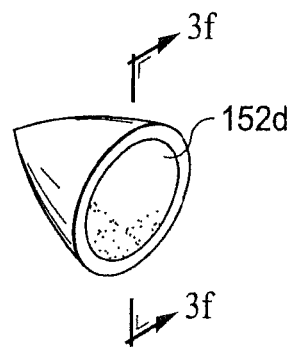
FIG. 3e is a perspective view illustrating an embodiment of a metering insert used with the lubrication system of FIGS. 2a, 2b, 2c, 2d, and 2e.
Figure 3F:
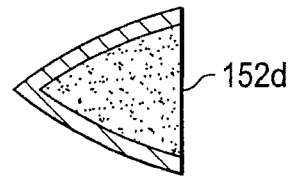
FIG. 3f is a cross-sectional view illustrating an embodiment of metering insert of FIG. 3e taken along line 3f-3f in FIG. 3e.
Figure 3G:
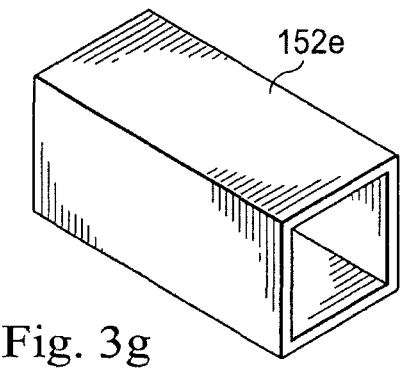
FIG. 3g is a perspective view illustrating an embodiment of a metering insert used with the lubrication system of FIGS. 2a, 2b, 2c, 2d, and 2e.
Figure 3H:
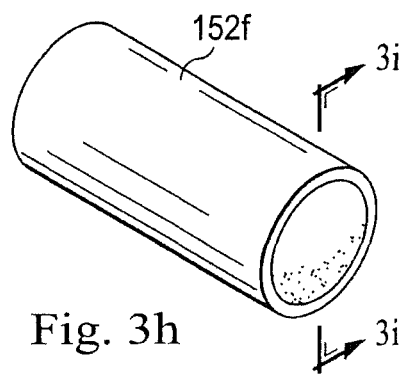
FIG. 3h is a perspective view illustrating an embodiment of a metering insert used with the lubrication system of FIGS. 2a, 2b, 2c, 2d, and 2e.
Figure 3I:
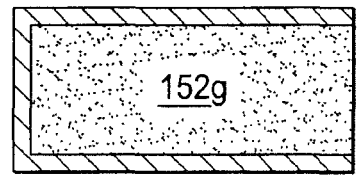
FIG. 3i is a cross-sectional view illustrating an embodiment of a metering insert used with the lubrication system of FIGS. 2a, 2b, 2c, 2d, and 2e.

Referring now to FIGS. 3a, 3b, 3c, 3d, 3e, 3f, 3g, 3h, and 3i, exemplary embodiments of metering inserts having various exemplary shapes, which may be the metering insert 152, are illustrated. As illustrated in FIG. 3a, a metering insert 152a may be generally shaped as a solid cylinder. As illustrated in FIG. 3b, a metering insert 152b may be generally shaped as a circular disk. As illustrated in FIGS. 3c and 3d, a metering insert 152c may be generally shaped as a hollow half sphere. As illustrated in FIGS. 3e and 3f, a metering insert 152d may be generally shaped as a hollow cone. As illustrated in FIG. 3g, a metering insert 152e may be generally shaped as a hollow rectangular box. As illustrated in FIG. 3h, a metering insert 152f may be generally shaped as a hollow cylinder. As illustrated in FIG. 3i, a metering insert 152g may be generally shaped as a hollow rectangular box or cylinder that is open on one end and closed on an end that opposes the open end. While a variety of different shapes and configurations of metering inserts have been described above, the present disclosure is not intended to be limited to the disclosed embodiments, and other embodiments or combinations of the disclosed embodiments, that provide other shapes and configurations are contemplated and may be selected for manufacturability, metering properties, durability, and/or other properties known in the art. Varying shapes may change the metering properties of metering insert 152. For example, solid, cylinder-shaped insert 152a may provide a lower flow rate as compared to disk shaped insert 152b. In another example, a first end of metering insert 152d may be open, providing more surface area for lubricant entering the first end as compared to an insert with a flat or solid first end.

The lubrication system 100 may also include a startup lubrication mechanism that is configured to rapidly provide an initial quantity of lubricant without metering to the pressurized fluid stream upon system startup. The provision of an initial quantity of lubricant, or bolus, to the pressurized fluid stream upon system startup provides immediate lubrication to the motor of the surgical instrument 10 and its adjacent supply line upon the installation of a new lubrication system 100 or upon the initial use of the surgical instrument 10. Incorporation of a startup lubrication mechanism, or pre-oiler, may help prevent premature failure or excessive wear of the surgical instrument 10.

Returning to FIG. 2c, an embodiment of a startup lubrication mechanism 154 includes a second lubricant delivery tube 156 that includes a third passage 158. The second delivery tube 156 includes a lower end that opens into the lubricant reservoir 146. An upper end of the second lubricant delivery tube 156 is in fluid communication with the second passage 142 at a location on the second passage 142 that is between the suction tap 134 and the metering portion 148.

Thus, the suction tap 134 is in fluid communication with the lubricant reservoir 146 along two paths—a first path that runs through the metering insert 152 and the first delivery tube 150, and a second path that runs through the third passage 158 of the second delivery tube 156.

In an embodiment, in operation, upon start up of the surgical instrument 10, a pressure differential is provided that pulls lubricant from the lubricant reservoir 146 through the third passage 158 of the second delivery tube 156, as this path offers less resistance than the path through the first delivery tube 150 and the metering insert 152. Thus, the second delivery tube 156 is operable upon startup of the system to provide a startup portion of lubricant. In the illustrated embodiment, the second delivery tube 156 opens into an upper portion of lubricant reservoir 146, and the start up portion of lubricant may be portioned, for example, by a portion of the lubricant reservoir 146 that is located above the upper portion of the lubricant reservoir 146 into which the second delivery tube 156 opens, as described in further detail below. In another embodiment, the second deliver tube 156 may extend further into the lubricant reservoir 146 than illustrated in FIG. 2d, and the start up portion of lubricant may be portioned, for example, according to how far the lower end of second delivery tube 156 extends into lubricant reservoir 146.

The lubricant reservoir 146 may include a main volume 160 that contains a to-be-metered portion of lubricant and an extended volume 162 that contains the startup portion of lubricant. The first and second delivery tubes 150 and 156 are both in fluid communication with main volume 160 of the lubricant reservoir 146. The startup portion of lubricant contained in the extended volume 162 is located above the point in the lubricant reservoir 146 at which the lower end of second delivery tube 156 accesses the lubricant reservoir 146. Thus, gravity and the pressure differential between the high pressure tap 136 and the upper end of second delivery tube 156 will quickly cause the startup portion of lubricant to enter the primary fluid path 124 through the suction tap 134 upon pressurized fluid flow through the primary fluid path 124.

Figure 2E:
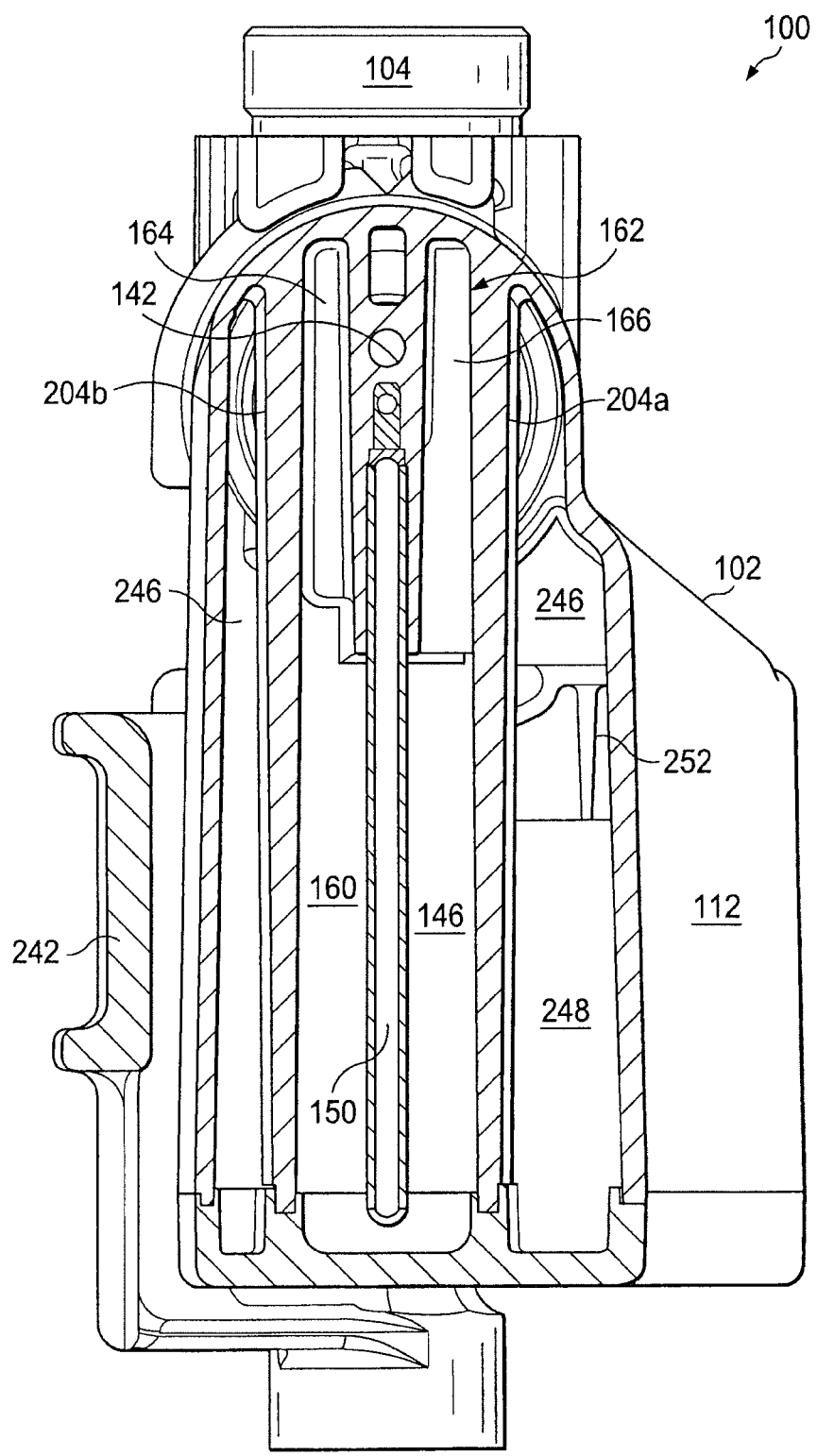
FIG. 2e is a cross-sectional view of the lubrication system of FIGS. 2a and 2b taken along line 2e-2e of FIG. 2b.

Referring now to FIG. 2e, a longitudinal cross-sectional view of the lubrication system 100 taken along line 2e-2e in FIG. 2b is illustrated. The extended volume 162 discussed above with reference to FIG. 2c may include a plurality of volumes. For example, a first extended volume 164 may be located on a first side of the second passage 142 and a second extended volume 166 may be located on a second side of the second passage 142 that is opposite the first side. A third extended volume 168, illustrated in FIG. 2d, may also contain a startup portion of lubricant, as described in further detail below. In an embodiment, approximately 0.25 grams of lubricant may be used as the startup portion of lubricant for pre-oiling the surgical instrument 10.

Returning to FIG. 2c, in operation, once the total amount of lubricant in the lubricant reservoir 146 drops below the point in the lubricant reservoir 146 at which the lower end of second delivery tube 156 accesses the lubricant reservoir 146, lubricant will then be supplied from main area 160 of reservoir 146 though first delivery tube 150 and the metering insert 152.

Figure 4A:
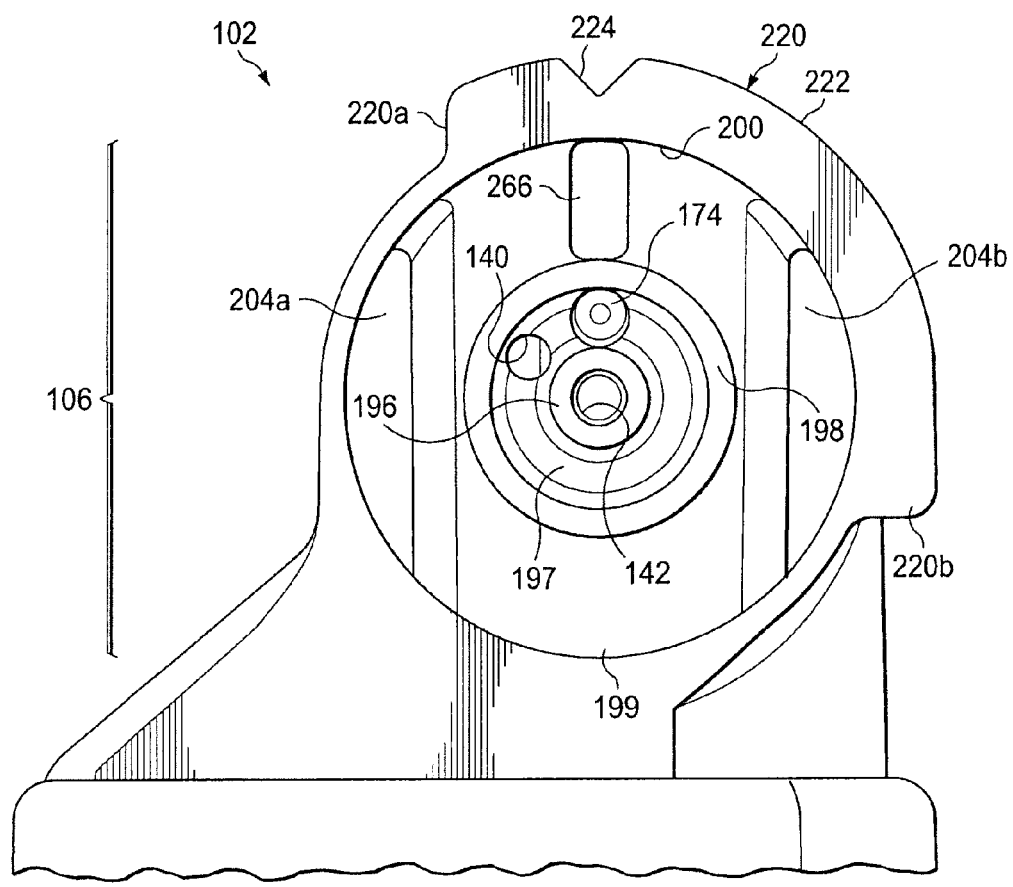
FIG. 4a is a front view illustrating an embodiment of a lubrication cartridge used in the lubrication system of FIGS. 2a, 2b, 2c, 2d, and 2e.
Figure 4B:
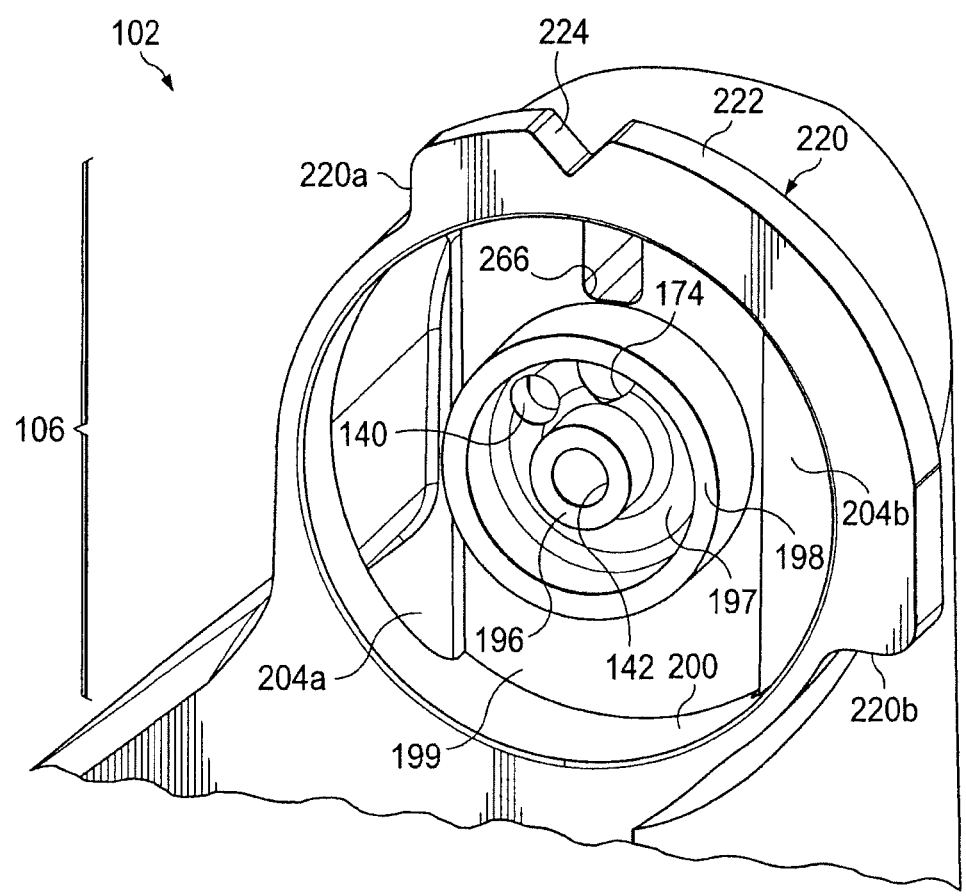

In an embodiment, a startup lubrication mechanism 170, which may be used with or without the startup lubrication mechanism 154, is illustrated in FIG. 2c. In the startup lubrication mechanism 170, a startup portion of lubricant may be stored in a horizontal containment tube 172. Referring briefly to FIG. 4a, the containment tube 172 may be in fluid communication with a high pressure area 197, the first passage 140 (illustrated in FIG. 2d), and the high pressure tap 136 (illustrated in FIG. 2c) through an opening 174 defined on a surface on the cartridge coupling 106 of the lubrication cartridge 102. From the opening 174, the containment tube 172 extends into lubrication cartridge 102, as illustrated in FIG. 2c. Thus, when the lubrication cartridge 102 is coupled to the stem 104, the startup portion of lubricant located in the containment tube 172 may travel (e.g., by the force of gravity) from the containment tube 172 and into the primary fluid path 124 through the high pressure tap 136, thereby supplying lubricant to the pressurized fluid, through the stem 104, the tubing 20, and to the surgical instrument 10 upon connection of the of the cartridge 102 to the stem 104, or upon startup of the surgical instrument 10.

In an embodiment, the containment tube 172 may be in fluid communication with the second passage 142, but sealed with respect to fluid communication with the first passage 140. Thus, gravity will quickly cause the startup lubricant located in the containment tube 172 to flow into the primary fluid path 124 through the second passage 142 and the suction tap 134.

Returning back to FIG. 2d, and as briefly described above, the third extended volume 168 may offer an additional containment volume for the startup portion of the lubricant, which may flow into the first passage 140 or into main area 160 of the lubricant reservoir 146. From the main area 160, the startup portion of the lubricant from the third extended volume 168 may enter the second passage 142 from either the first or second delivery tubes 150 or 156.

Various system properties may affect the lubricant flow rate such as, for example, the pressure differential between the first and second passages 140 and 142, the lubricant viscosity, and the density of the metering insert 152. In an embodiment, the pressure differential may be at least partially established through the selection of suitable diameters for the first, second, and third passages 140, 142, and 158. In embodiments which use the startup lubrication mechanism 154 with second delivery tube 156, a short circuiting of the pressurized fluid after evacuation of the startup portion of the lubricant may be prevented, or mitigated, by sizing the third passage 158 correctly. For example, by sizing the third passage 158 with a diameter that is effectively smaller than the diameter of the first passage 140, a pressure differential may be preserved across the metering insert 152. In an embodiment, the first and third passages 140 and 158 have a diameter ratio designed to maintain a pressure differential in the range of about 1 psi to about 5 psi, which may provide a sufficient pressure differential to pull lubricant through the metering insert 152 after evacuation of the startup portion of the lubricant from the lubrication cartridge 102.

The lubricant viscosity and the density of the metering insert 152 may also affect the pressure differential. The average pore size in the metering insert 152 may be adjusted to obtain a desired lubricant flow rate and may be limited by the viscosity of the lubricant. In an embodiment, flow through the metering insert 152 may be controlled by varying processing parameters during manufacture of the metering insert. Thus, by controlling the porosity, or density, and the average pore size, lubricant metering during use of the surgical instrument 10 can be reliably controlled. Repeatable accuracy may be significantly improved over conventional orifice-style metering mechanisms.

Figure 4C:
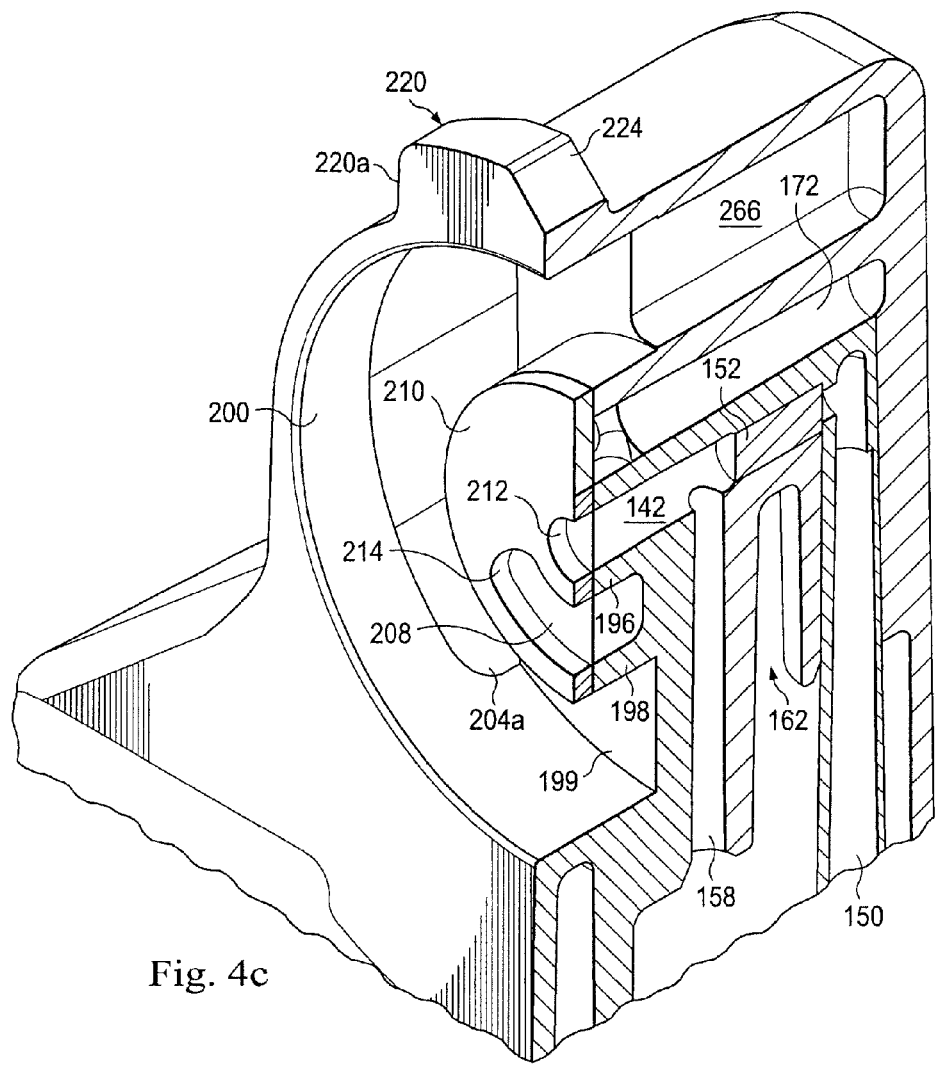
Figure 5A:
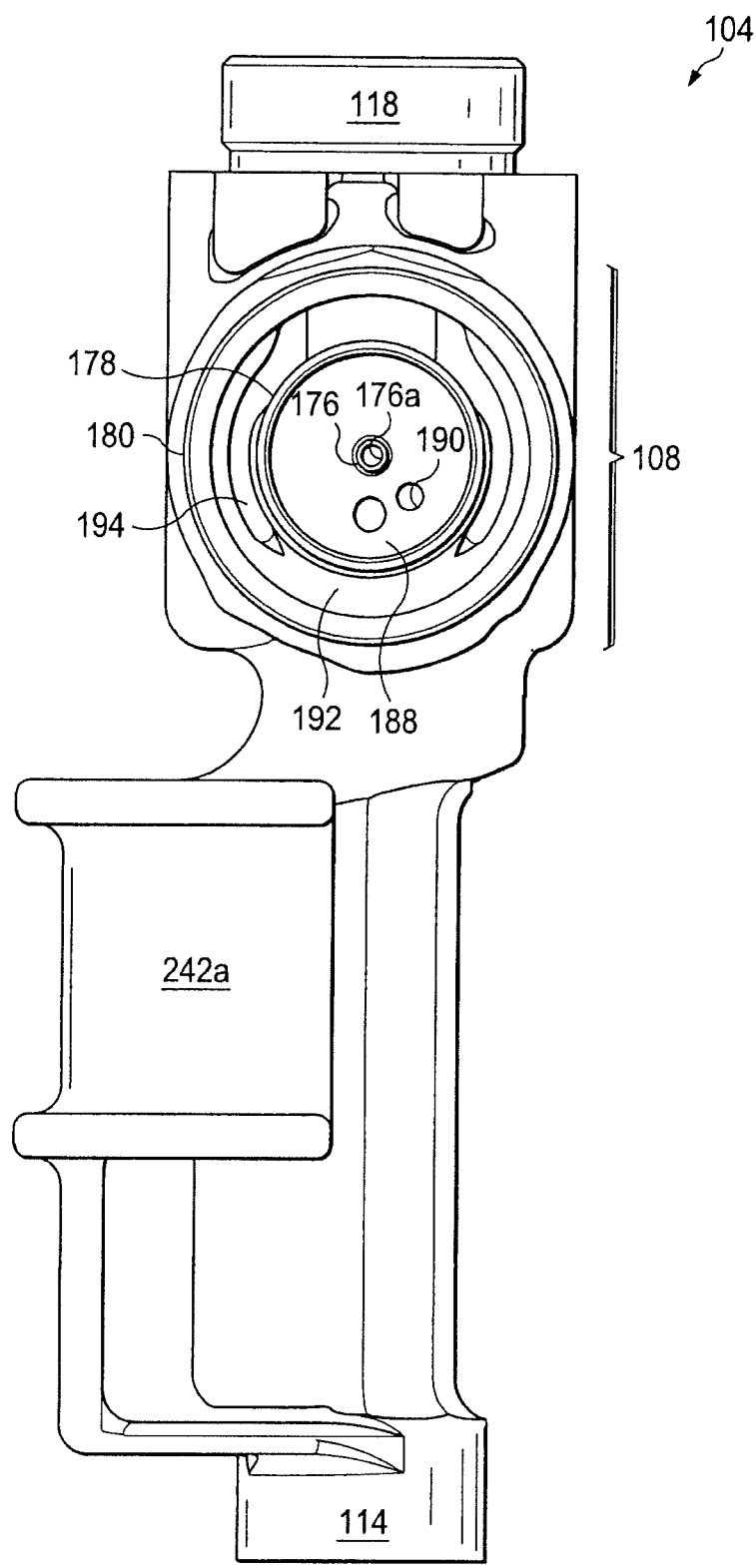
FIG. 5a is a front view illustrating an embodiment of a stem used in the lubrication system of FIGS. 2a, 2b, 2c, 2d, and 2e.
Figure 5B:
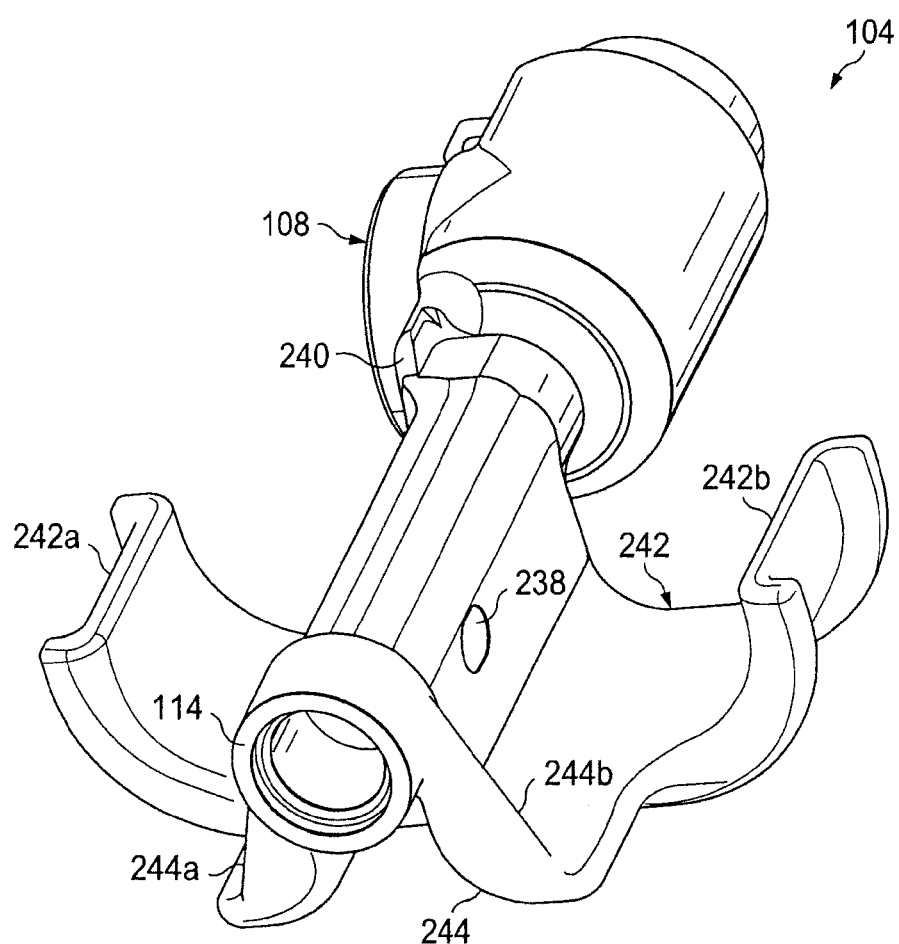
Figure 6A:
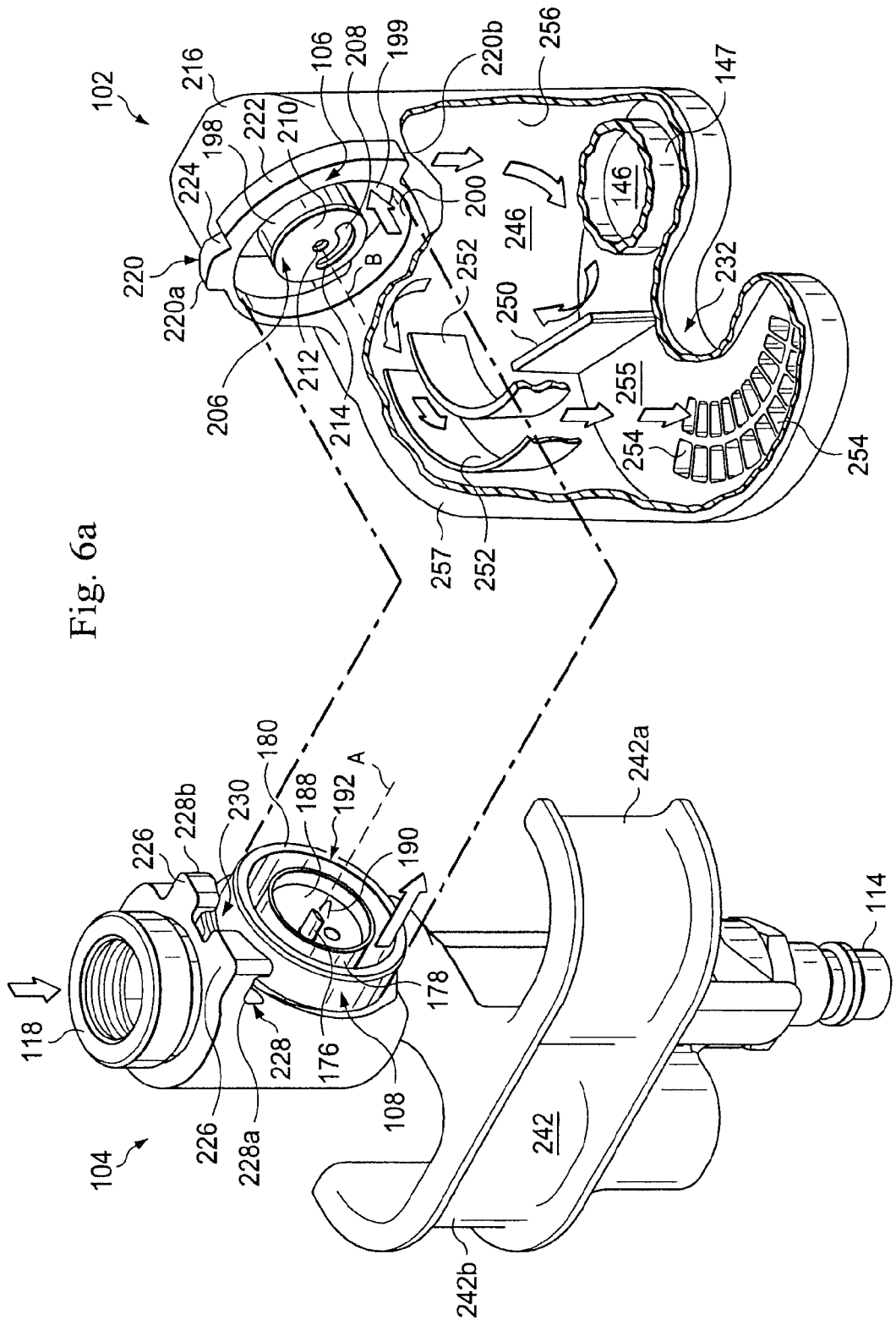
FIG. 6a is a cut-away perspective view illustrating the lubrication cartridge of FIGS. 4a, 4b, 4c, and 4d, and the stem of FIGS. 5a and 5b.
Figure 6B:
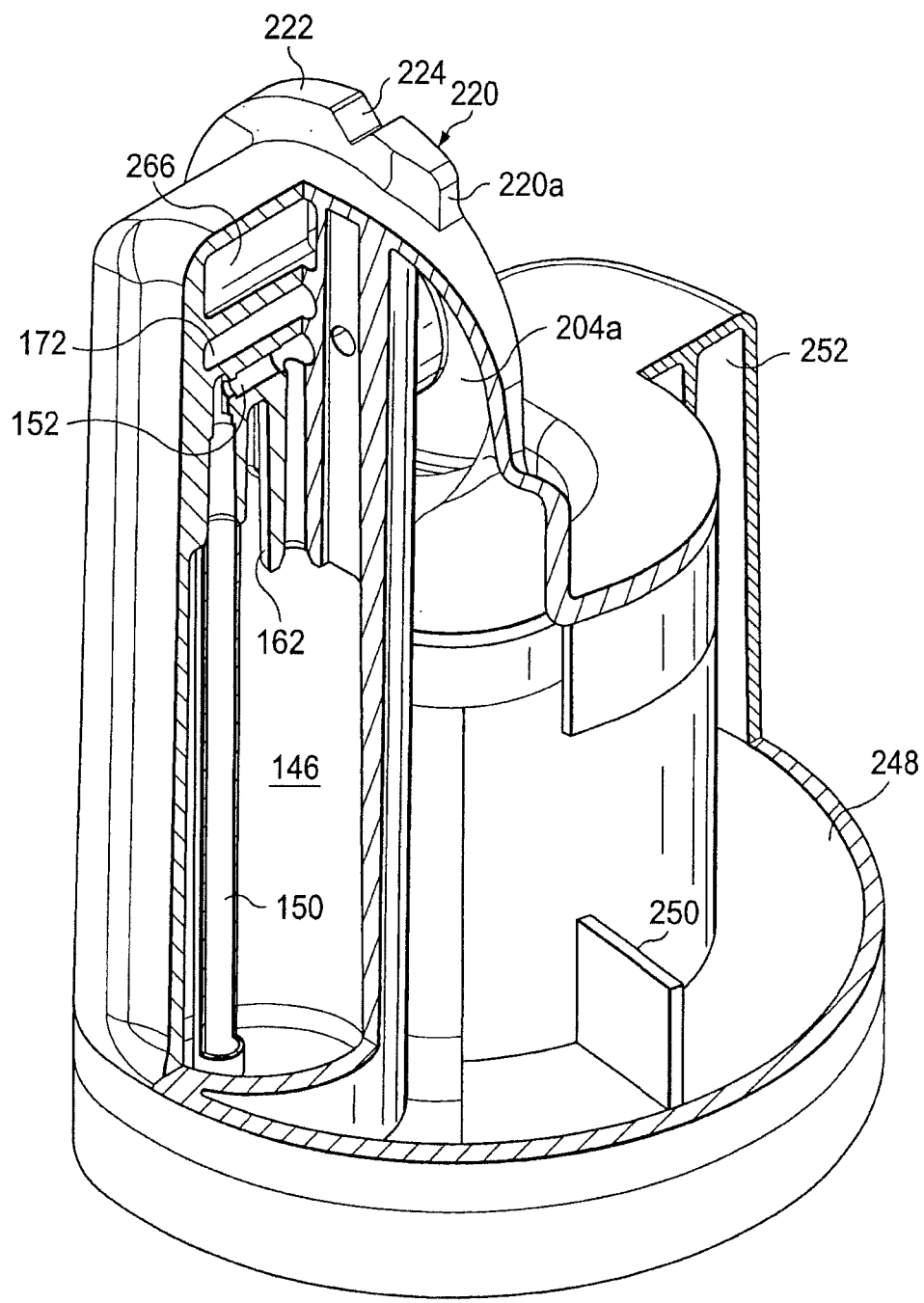
FIG. 6b is a cut-away perspective view illustrating the lubrication system of FIGS. 2a, 2b, 2c, 2d, and 2e.

Referring now to FIGS. 4a, 4b, 4c, 5a, and 6a, the cartridge coupling 106 on the lubrication cartridge 102 and the stem coupling 108 on the stem 104 are described in further detail. FIGS. 5a and 6a illustrate the stem coupling 108 that includes a coaxial wall configuration with a center annulus wall 176, an intermediate annulus wall 178, and an outer annulus wall 180 that each extend from a surface of the stem coupling 108 and that are located in a generally concentric orientation about an axis A. The center annulus wall 176 includes a piercing cannula that extends along the axis A and may include a sharpened tip. The center annulus wall 176 defines a passage 176a that is in fluid communication with the suction tap 134 (described above with reference to FIG. 2c). The intermediate annulus wall 178 and the center annulus wall 176 define a high pressure area 188 between them that is in fluid communication with the high pressure tap 136 (described above with reference to FIG. 2c). A piercing pin 190 extends from the surface of the stem coupling 108 that is located in the high pressure area 188. The outer annulus wall 180 and the intermediate annulus wall 178 define a reduced-pressure exhaust area 192 between them.

In operation, a greater volume of exhaust fluid may return from the surgical instrument 10 than was supplied as pressurized fluid to the surgical instrument 10 due to, for example, a volumetric increase that may be caused by the desired expansion of the pressurized fluid to power the surgical instrument 10. In order to accommodate the greater volume of exhaust fluid, the stem coupling 108 may include one or more openings with a combined cross-sectional area that is larger than the cross-sectional area included through primary fluid path 124. For example, a crescent-shaped opening 194 may be provided on the surface of the stem coupling 108 in the reduced-pressure exhaust area 192 to provide fluid communication between the reduced-pressure exhaust area 192 and the exhaust passage 138.

FIGS. 4a, 4b, 4c, and 6a illustrate the cartridge coupling 106 that includes a coaxial wall configuration with a center annulus wall 196, an intermediate annulus wall 198, and an outer annulus wall 200 that each extend from a surface of the cartridge coupling 106 and that are located in a generally concentric orientation about an axis B. The center annulus wall 196 provides an entrance to the second passage 142, described above with reference to FIG. 2c, when the lubrication cartridge 102 is coupled to the stem 104. The intermediate annulus wall 198 and the center annulus wall 196 define a high pressure area 197 between them that is in fluid communication with the first passage 140 an immediately adjacent the high pressure area 188 on the stem coupling 108 when the lubrication cartridge 102 is coupled to the stem 104. The outer annulus wall 200 and the intermediate annulus wall 198 define a reduced-pressure exhaust area 199 between them that is immediately adjacent the reduced-pressure area 197 on the stem coupling 108 when the lubrication cartridge 102 is coupled to the stem 104.

In operation, in order to accommodate the greater volume of exhaust fluid that returns from the surgical instrument 10, described above with reference to FIGS. 1a and 1b, the cartridge coupling 106 may include one or more openings with a combined cross-sectional area that is larger than the cross-sectional area provided through primary fluid path 124. For example, two large, semicircular openings 204a and 204b are defined on the surface of the cartridge coupling 106 in the reduced-pressure exhaust area 199 and provide fluid communication between the reduced-pressure exhaust area 192 and the exhaust portion 112 of the lubrication cartridge 102.

Figure 4D:
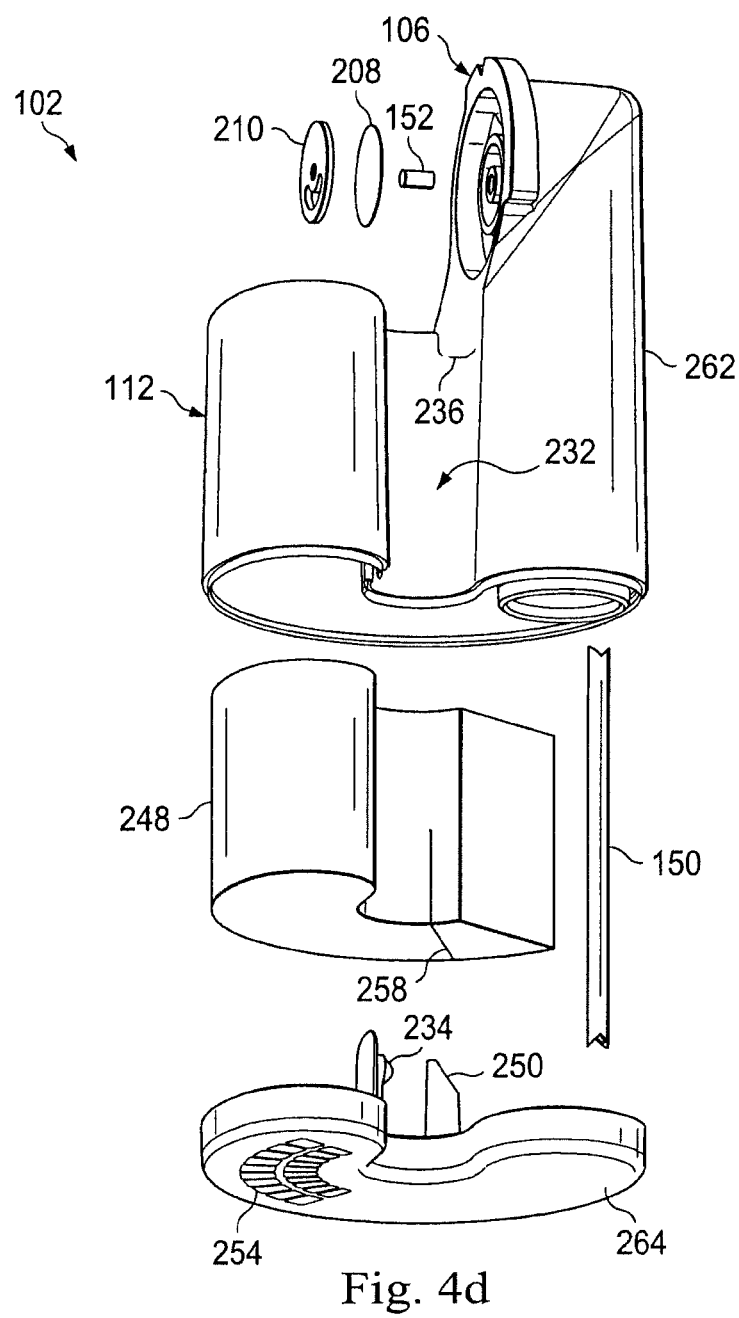

Referring now to FIGS. 4c, 4d, and 6a, the lubrication cartridge 102 and the stem assembly 104 will be described in further detail. A seal assembly 206 for a portion of the cartridge coupling 106 may include a frangible seal 208 and a sealing gasket 210. The seal 208 may be sized to match the outer diameter of the intermediate annulus wall 198 so as to span the high pressure area 197 and the entrance to the second passage 142. The seal 208 may function to seal lubricant such as, for example, the startup portion of lubricant described above, inside the lubrication cartridge 102. The seal 208 and the sealing gasket 210 may cooperatively function to maintain and preserve separate pressure areas such as, for example, the second passage 142, the high pressure area 197, and/or the reduced-pressure exhaust area 199. The sealing gasket 210 may define a centrally located aperture 212 and an intermediate opening 214 that correspond to features on both the cartridge coupling 106 and the stem coupling 108, as will be described in further detail below.

In an embodiment, the frangible seal 208 includes a metal foil that is sealed to the center and intermediate annulus walls 196 and 198 with an adhesive or other sealing mechanism known in the art. In an embodiment, the seal 208 may include an aluminum foil that is approximately 0.002" thick. The sealing gasket 210 may include a thin material that is slightly compressible such as, for example, Teflon, rubber, closed cell foam, and/or a variety of other gasket materials known in the art, in order to provide a seal between the lubrication cartridge 102 and the stem 104 when lubrication system 100 is assembled.

In an embodiment, the seal 208 may include a plug (not illustrated) that may be fabricated from, for example, an elastomeric material. The plug may be designed to seal lubricant in the cartridge 102 during shipping and storage by blocking the first passage 140 such that lubricant cannot escape from the lubricant reservoir 146. In such an embodiment, the seal 208 may sealingly cover the entrance to the second passage 142 only and the piercing pin 190 may be eliminated. In assembly operation, when the cartridge coupling 106 on the lubricant cartridge 102 is coupled to the stem coupling 108 on the stem 104, the piercing cannula on the center annulus wall 176 pierces the seal 208 to provide access to the second passage 142, and high pressure fluid entering the first passage 140 through the high pressure area 197 may dislodge the plug. In an embodiment, the plug may be dislodged into the lubricant reservoir 146. In an embodiment, the plug or seal 208 may be replaced with a burst disk, check valve, flapper, and/or a variety of other sealing devices known in the art. In addition to the sealing function described above, the seal 208 may provide a tamper-proofing function.

Referring now to FIGS. 4a, 4b, 4c, 4d, 5a, 5b, 6a, 6b, 6c, 6d, 6e, 6f, 6g, and 6h, various features of the cartridge 102 and the stem 104 will be described. The lubrication cartridge 102 includes an outer surface 216 that is located adjacent the cartridge coupling 106. A locking tab 220 may be located between the cartridge coupling 106 and the outer surface 216 of the lubrication cartridge 102. The locking tab 220 includes an outer surface 222 that extends along the length of the locking tab 220. The locking tab 220 may include a consistent width along its length or may have a width that tapers from a narrower leading edge 220a to a wider trailing edge 220b. The locking tab 220 may define a locking indention 224.

The stem 104 includes a retaining member 226 that is located adjacent the stem coupling 108 and defines a groove 228 along its length. The groove 228 may be keyed to slidingly receive the locking tab 220 on the lubrication cartridge 102. The groove 228 may have a width that is consistent along its length or may have a width that tapers from a wider width at a first end 228a of the groove 228 to a narrower width at a second end 228b of the groove 228. An open section 230 may also be defined by the retaining member 226.

The lubrication cartridge 102 may include a variety of features which aid in securing the cartridge 102 and to the stem 104. In an embodiment, the lubrication cartridge 102 may define a longitudinal recess 232 that allows the lubrication cartridge 102 to partially wrap around the stem 104, which helps to reduce the size profile of the lubrication system 100. The lubrication cartridge 102 may also include a securing tab 234 and define a coupling support recess 236.

The stem 104 similarly includes a variety of features which are complimentary with those of the lubrication cartridge 102 described above, along with some additional features. In an embodiment, the stem 104 defines a detent 238 that cooperates with the securing tab 234 on the lubrication cartridge 102, as will be described in further detail below. The stem 104 may also include a coupling support projection 240 that cooperates with the coupling support recess 236, as will be described in further detail below.

In order to protect the lubrication cartridge 102 from accidental bumps and disruptions which could cause its uncoupling from the stem 104, the stem 104 may include a kick guard 242 and a lower support 244. The kick guard 242 may include left and right contoured wings 242a and 242b that extend from the stem 104. The lower support 244 may include left and right webs 244a and 244b, each extending between portions of the stem 104 and the left and right contoured wings 242a and 242b, respectively, of the kick guard 242. In an embodiment, the lower support 244 may function solely as a protective shield. In an embodiment, the lower support 244 may function as a friction engagement device to help secure the lubrication cartridge 102, and it may include other securing features such as, for example, tabs, detents, and/or a variety of other securing features known in the art. In an embodiment, the kick guard 242 and the lower support 244 may be integral to each other and removably attachable to the stem 104. In an embodiment, the kick guard 242 and the lower support 244 may be separate from the stem 104 and separate from each other. In an embodiment, the kick guard 242 and the lower support 244 may be absent from the stem 104 and/or the lubrication system 100.

Figure 6C:
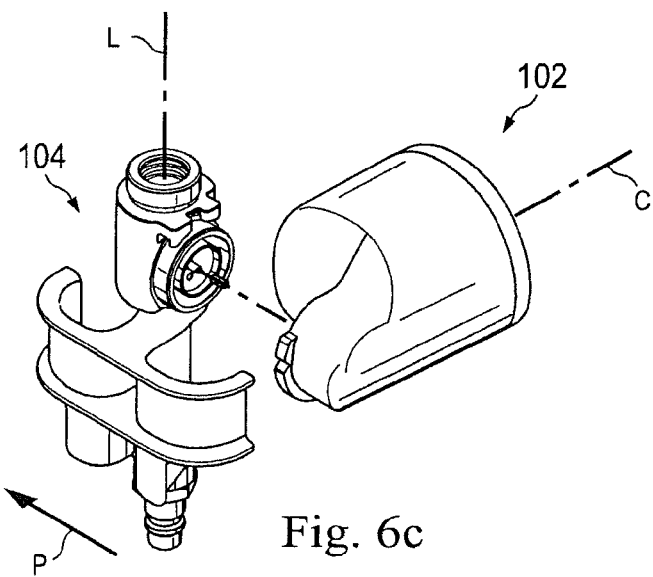
FIG. 6c is a perspective view illustrating an embodiment of the lubrication cartridge of FIGS. 4a, 4b, 4c, and 4d being coupled to the stem of FIGS. 5a and 5b and in an initial coupling orientation.
Figure 6D:
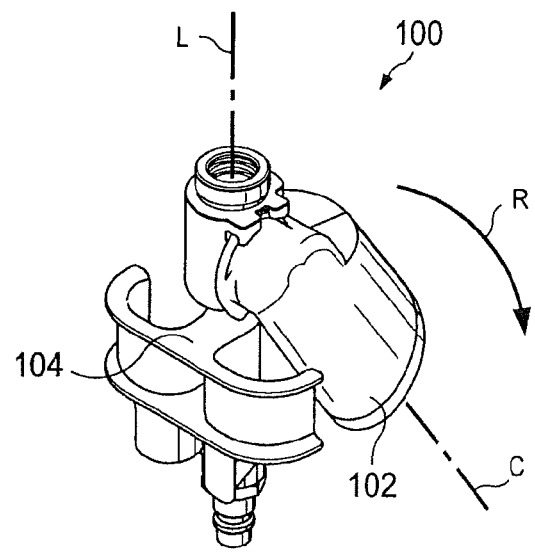
FIG. 6d is a perspective view illustrating an embodiment of the lubrication cartridge of FIGS. 4a, 4b, 4c, and 4d being coupled to the stem of FIGS. 5a and 5b and in an intermediate coupling orientation.
Figure 6E:
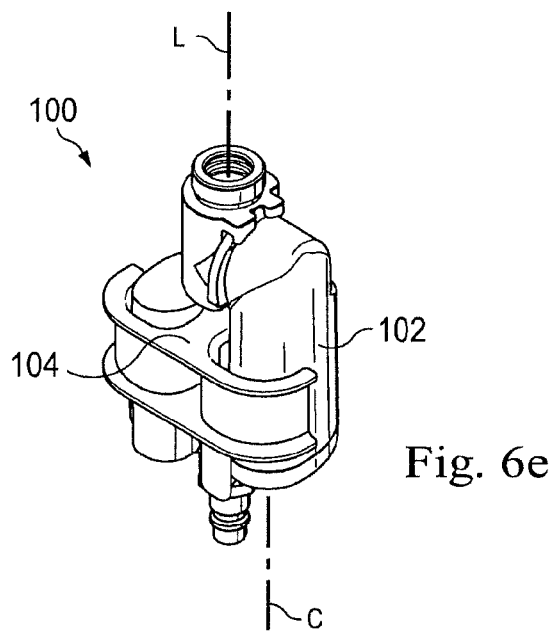
FIG. 6e is a perspective view illustrating an embodiment of the lubrication cartridge of FIGS. 4a, 4b, 4c, and 4d coupled to the stem of FIGS. 5a and 5b and in a final coupling orientation.

FIGS. 6c, 6d, and 6e illustrate a variety of coupling orientations of the lubrication cartridge 102 relative to the stem 104 in order to illustrate the assembly of the lubrication system 100. Referring now to FIG. 6c, the lubrication cartridge 102 and the stem 104 are shown in an initial coupling orientation, with the stem 104 generally aligned along its axis L and the cartridge 102 generally aligned along an axis C that is generally perpendicular to the axis L when the lubrication cartridge 102 and the stem 104 are in the initial coupling orientation. In the initial coupling orientation, the lubrication cartridge 102 and the stem 104 are positioned such that the axis A of the stem coupling 108 and the axis B on the cartridge coupling 106 (illustrated in FIG. 6a) are generally co-linear. The lubrication cartridge 102 may then be moved relative to the stem 104 in a direction P such that the cartridge coupling 106 engages the stem coupling 108. When the cartridge coupling 106 engages the stem coupling 108, the outer annulus wall 200 on the cartridge coupling 106 slidingly contacts the outer annulus wall 180 on the stem coupling 108, the piercing cannula on the center annulus wall 176 passes through the centrally located aperture 212 defined by the sealing gasket 210 and punctures the seal 208, and the piercing pin 190 passes through intermediate opening 214 defined by the sealing gasket 210 to puncture the seal 208. Thus, the piercing cannula on the center annulus wall 176 opens the second passage 142 in the lubrication cartridge 102 to the suction tap 134 in the stem 104, and the piercing pin 190 opens the high pressure areas 188 and 197 between the first passage 140 on the stem 104 and the high pressure tap 136 on the lubrication cartridge 102.

Referring now to FIG. 6d, the lubrication system 100 is illustrated with the lubrication cartridge 102 and the stem 104 in an intermediate coupling orientation. As illustrated, the lubrication cartridge 102 has been rotated relative to the stem 104 in a direction R after the engagement of the cartridge coupling 106 and the stem coupling 108 discussed above. As the lubrication cartridge 102 is rotated relative to the stem 104 in the direction R, the locking tab 220 on the lubrication cartridge 102 enters the groove 228 defined on the stem 104 and prevents the cartridge coupling 106 and the stem coupling 108 from becoming disengaged. In addition, as lubrication cartridge 102 is rotated relative to the stem 104 in the direction R, the piercing pin 190 travels through the intermediate opening 214 defined by the sealing gasket 210 and tears a semicircular opening in the seal 208, thereby further providing fluid communication across the high pressure areas 188 and 197. In an embodiment, a tapered width of either or both of the locking tab 220 and/or the groove 228 may facilitate the entry of the leading edge 220a of the locking tab 220 into the first end 228a of the groove 228, and may be designed to increase the coupling forces that keep the cartridge coupling 106 and the stem coupling 108 engaged and/or provide a friction fit to resist disengaging rotation of cartridge 102 relative to the stem 104.

Figure 6F:
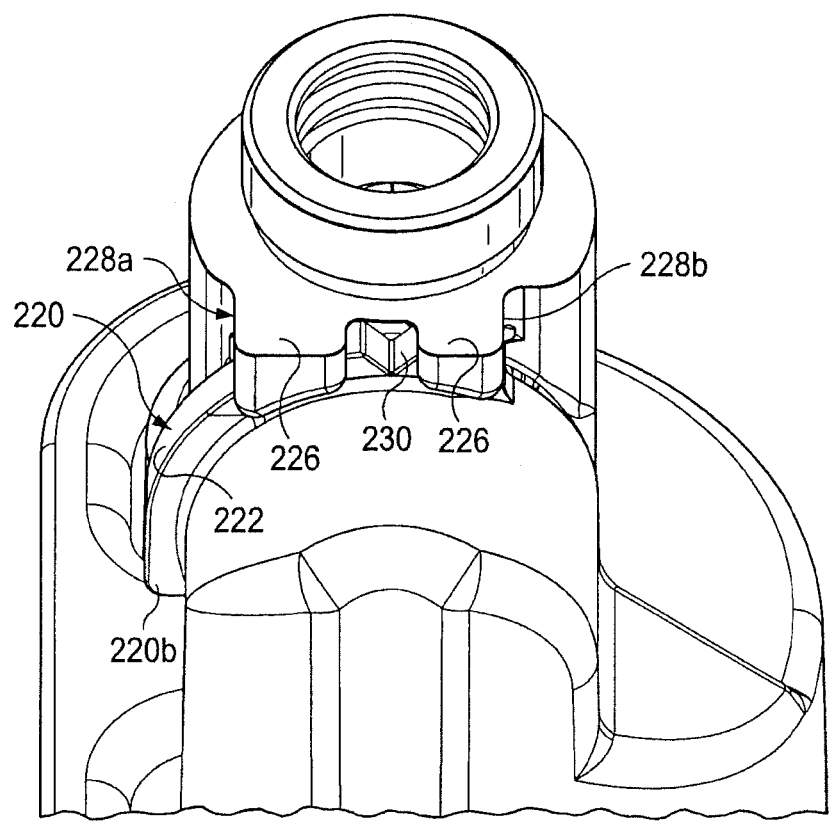
FIG. 6f is a perspective view illustrating the lubrication cartridge of FIGS. 4a, 4b, 4c, and 4d coupled to the stem of FIGS. 5a and 5b the final coupling orientation.
Figure 6G:
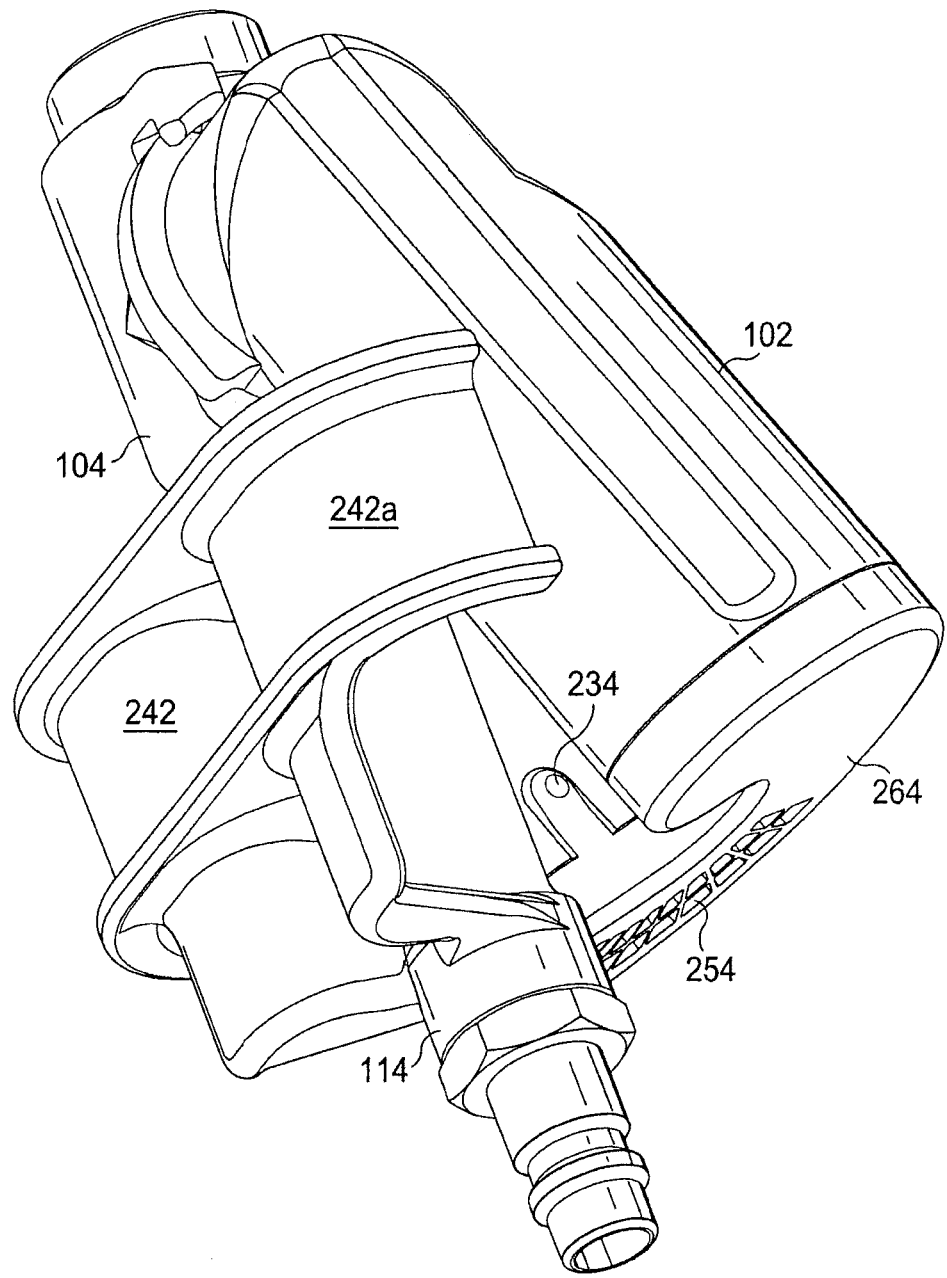
FIG. 6g is a perspective view illustrating an embodiment of the lubrication cartridge of FIGS. 4a, 4b, 4c, and 4d being coupled to the stem of FIGS. 5a and 5b and in the intermediate coupling orientation.
Figure 6H:
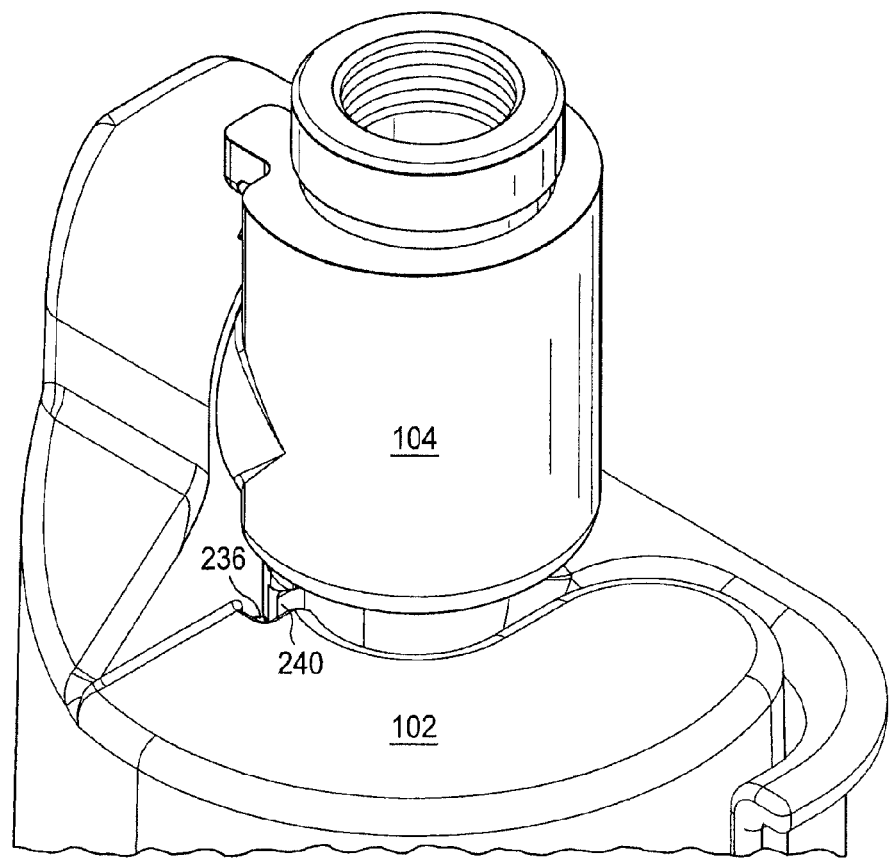
FIG. 6h is a perspective view illustrating an embodiment of the lubrication cartridge of FIGS. 4a, 4b, 4c, and 4d coupled to the stem of FIGS. 5a and 5b and in the final coupling orientation.

Referring now to FIG. 6e, the lubrication system 100 is illustrated with the lubrication cartridge 102 and the stem 104 in an final coupling orientation. As illustrated, the lubrication cartridge 102 has been fully rotated in the direction R, illustrated in FIG. 6d, such that it is installed on stem 104 and the lubrication system 100 is ready for use. In this final coupling orientation, the axis L and the axis C are generally parallel to each other. Thus, a quarter-turn coupling lubrication system 100 is provided in which the lubrication cartridge 102 is rotated relative to the stem 104 approximately 90 degrees in order to secure the lubrication cartridge 102 to the stem 104. As the lubrication cartridge 102 is rotated into the final coupling orientation, various features described above may cooperate to further secure the lubrication cartridge 102 to the stem 104. For example, the securing tab 234 on the lubrication cartridge 102 may elastically deform slightly during the coupling of the lubrication cartridge 102 and the stem 104 before becoming positioned in the detent 238 defined by the stem 104. In an embodiment, the securing tab 234 may provide an audible and/or tactile feedback to a user that the lubrication cartridge 102 is fully engaged with, and secured to, the stem 104. In order to further and more evenly compress the sealing gasket 210 between the intermediate annulus walls 178 and 198 and the center annulus walls 176 and 196, the coupling support projection 240 on the stem 104 may engage the coupling support recess 236 defined by the lubrication cartridge 102, as illustrated in FIG. 6h. In an embodiment, the locking indentation 224 in the locking tab 220 on the lubrication cartridge 102 may be viewable by a user through the open section 230 in the retainer member 226 to indicate that the lubrication cartridge 102 is fully secured to the stem 104, as illustrated in FIG. 6f. The positioning of the locking tab 220 in the retainer member 226 and the engagement of the coupling support projection 240 and the coupling support recess 236 may help to retain the lubrication cartridge to the stem 104 axially during internal pressurization.

In an embodiment, a clip or other protrusion may physically engage the locking indentation 224 through the open section 230. Such a clip or protrusion may be adjustably coupled to stem 104 or may extend from a coaxial supply line coupling receivable by the coupling 118.

In addition to other benefits described herein, the lubrication system 100 may also provide an ergonomic and safety advantage over conventional lubrication systems. Referring to FIGS. 6c, 6d, and 6e, only a relatively small force in the direction P may be required to engage cartridge coupling 106 and the stem coupling 108. Thereafter, a rotation force in the direction R may be supplied with only the palm of a user's hand. Thus, combined pressing and threading motions that require a relatively large gripping force and repetitive wrist rotation by a user may be minimized or avoided. The quarter-turn coupling lubrication system 100 may also be safer in situations where a gripping force by a user is not easily obtainable on a lubrication cartridge that is to be attached or removed because, for example, a gloved hand may be wet or slippery due to operating room conditions.

Referring now to FIGS. 2c, 2d, 2e, 4a, 4b, 4c, 4d, 5a, 6a, and 6b, various features and operation of the exhaust portion 112 of the lubrication cartridge 102 will be further described below. The exhaust portion 112 may generally comprise a low velocity plenum 246 (illustrated in FIGS. 2e and 6a) that is in fluid communication with the exhaust area 199 on the cartridge coupling 106 through the semicircular openings 204a and 204b. In an embodiment, a filter 248 (illustrated in FIGS. 2c, 2d, 4d, and 6b) may be housed in the exhaust portion 112. In an embodiment, the filter 248 may include a cellulose filter material or other suitable filter media such as, for example, foam, wool, felt, porous plastics, porous metals, and/or a variety of other filter materials known in the art. The plenum 246 generally occupies various volumes inside the cartridge 102 that are not occupied by the lubrication portion 110. The exhaust portion 112 may include a baffle wall 250 and a plurality of vanes 252, and may define a plurality of exhaust holes 254. The baffle wall 250 extends vertically upwards into the plenum 246 from a bottom wall 255 of the lubrication cartridge 102, and the vanes 252 extend vertically downward into the plenum 246 from an upper wall 257 of the lubrication cartridge 102. The exhaust holes 254 are defined by the bottom wall 255 of lubrication cartridge 102 and located downstream of the baffle wall 250 in the exhaust fluid flow.

In operation, reduced-pressure exhaust fluid enters the stem 104 and travels through the outer bore 122. The exhaust fluid then passes through the exhaust passage 138 and the crescent shaped void 194 to reach the reduced-pressure exhaust areas 192 and 199 located between the outer annulus walls 180 and 200 and intermediate annulus walls 178 and 198 on the stem 104 and the lubrication cartridge 102, respectively. The exhaust fluid then enters the plenum 246 of the exhaust portion 112 in the lubrication cartridge 102 through the semicircular openings 204a and 204b.

As illustrated by flow arrows in FIG. 6a, the exhaust fluid entering the plenum 246 through the semicircular openings 204a and 204b is deflected downwards by a back wall 256 of the lubrication cartridge 102. Each abrupt change of direction of the exhaust fluid in the exhaust portion 112 causes lubrication carried by the exhaust fluid (e.g., oil mist and droplets) to fall out of the exhaust fluid, while relative increases in the flow area cause reductions in velocity of the exhaust fluid, further promoting the lubrication to fall out of the exhaust fluid. Reductions in the velocity of the exhaust fluid may also decrease exhaust noise and increase filtering efficiency. The exhaust fluid flows adjacent the back wall 256 until its flow direction is abruptly forced to change by the bottom wall 255 of the lubrication cartridge 102 and then again by the baffle wall 250. As the exhaust fluid is forced to effectively reverse direction, more lubricant carried in the exhaust fluid may fall out of the exhaust fluid upstream from the baffle wall 250. In addition, the exhaust filter 248 (described above with reference to FIG. 4b) may straddle the baffle wall 250 at a slit 258 (illustrated in FIG. 4d) such that the exhaust fluid directed by the baffle wall 250 passes through at least a portion of the exhaust filter 248.

The exhaust fluid is then redirected along the vanes 252 into the filter 248 before exiting the lubrication cartridge 102 through the exhaust holes 254. The movement of the exhaust fluid through the exhaust portion 112 of the lubrication cartridge 102 provides an efficient and comprehensive technique for separating lubricant from the exhaust fluid prior to releasing the exhaust fluid into an operating room environment. In an embodiment, the vanes 252 may be designed and positioned to direct and divide the exhaust fluid for more efficient filtering. As illustrated in FIGS. 2c and 2d, a head space 260 that is defined between the vanes 252 and located above the filter 248 may function to provide a less resistive flow path for the exhaust fluid. By having the baffle wall 250 extend into the slit 258 on the filter 248, the exhaust fluid may be directed to pass through filter 248 twice-once on the upstream side of the baffle wall 250 and once on the downstream side of the baffle wall 250.

In an embodiment, some or all of the lubrication system 100 such as, for example, the lubrication cartridge 102, may be designed as a single-use, disposable member. To the extent that lubrication cartridge 102 is designed to be used only once, the locking tab 220, the flexible securing tab 234, and/or other securing feature may be designed as frangible retainers such that upon decoupling of the lubrication cartridge 102 from the stem 104 after use, the frangible retainer is broken off or otherwise functionally impaired to render the lubrication cartridge 102 unusable. In an embodiment, the stem 104 may be designed as a reusable, capital component.

The lubrication cartridge 102 may include recycled materials and may itself be recyclable. In an embodiment, the stem 104 may also include a disposable design. Thus, the lubrication system 100 may comprise the stem 104, the lubrication cartridge 102, and/or other components which may be reusable or disposable. In an embodiment, the lubrication cartridge 102 is reusable, but the metering insert 152 is disposable, and may be user-replaceable.

In an embodiment, one of the stem coupling 108 and the cartridge coupling 106 may comprise a universal coupling capable of interfacing with stems or lubrication cartridges from different suppliers. In addition, an adapter may be provided separately, or as part of a system which may retrofit a non-compliant stem coupling for use with a lubrication cartridge having a coupling configured according to an embodiment disclosed herein.

An additional benefit is obtained by the teachings of the present disclosure by moving the lubricant metering from an expensive, reusable part of the assembly, as practiced in conventions systems, to a disposable part of the lubrication system 100. A typical single- or multi-orifice metering device may require the orifices to be precisely machined within narrow tolerances to be effective. Such small and precise orifices may easily become plugged leading to costly tool damage or surgical delays. A sintered metal metering insert may offer significant savings over the cost to manufacture a single- or multi-orifice metering device along with greater reliability during usage. Thus, a single- or multi-orifice metering device, which is typically a costly component of a reusable capital-type stem or stem assembly, may be economically eliminated. And moving the metering function to a disposable cartridge using a metering insert, as described herein, may also reduce the maintenance required to obtain reliable lubricant metering.

Additional cost benefits may be provided through certain design-for-manufacturing aspects of the novel device described above. In an embodiment, the stem 104 is a single body component to which standard supply line fittings are coupled. The stem 104 may have a main body that is generally produced by casting and may or may not require additional machining. The piercing cannula on the center annulus wall 176 and the piercing pin 190 may be a part of the single-component stem body or may be inserts added during assembly. In addition, the piercing cannula on the center annulus wall 176 or the piercing pin 190 may represent wear components that may be replaceable separately from the main body of the stem 104.

Referring now to FIG. 4d, the lubrication cartridge 102 may include a body portion 262 and a cap portion 264. During assembly, the first delivery tube 150, the exhaust filter 248, and the metering insert 152 may be pressed into their respective locations in the body portion 262. The cap portion 264, which may include a butt joint (not illustrated), may be, for example, sonically welded to the body portion 262.

Lubricant may be added to the lubrication cartridge 102 before or after attachment of the cap portion 264. In addition, the gasket 210 and the seal 208 may be added to the lubrication cartridge 102 before or after lubricant is added to the lubrication cartridge 102 to prevent the lubricant from leaking prior to installation on the stem 104. In other embodiments, the lubrication cartridge 102 may be completely assembled without lubricant, and may be filled with lubricant (e.g., via a needle) before or after attachment of seal 208, through a sealable port (not illustrated).

In an embodiment, the lubrication cartridge 102 may be injection molded to include some or all of the internal passages and features described above. Other manufacturing processes such as, for example, casting, stereolithography, and/or a variety of other manufacturing processes known in the art, may be used. The body portion 262 and the cap portion 264 may include polycarbonate selected for strength, weldability, and moldability. The first delivery tube 150 may include polypropylene. Other suitable materials such as, for example, stainless steel, titanium, shape memory alloys, polymers, carbon fiber, porous materials, and/or a variety of other materials known in the art, are contemplated for one or all of the parts and features included in this system. In addition, other suitable joining methods, manufacturing methods, and assembly sequences are contemplated for one or all of the parts and features included in the lubrication system 100.

In order to limit accidental lubricant spills after the seal 208 has been punctured, the disclosed embodiments and their equivalents may include spill resistant design features. For example, a combination of horizontal and vertical passages may be arranged to reduce spillage when the lubrication cartridge 102 is either vertically or horizontally positioned. In an embodiment, the first, second, and third extended areas 164, 166, and 168 in the lubrication cartridge 102 may be designed and arranged to contain the usage portion of lubricant if then lubrication cartridge 102 is turned on its side. The first and second passages 140 and 142 may be oriented such that they are substantially vertical if the lubrication cartridge 102 is tipped on its side or if the first and second delivery tubes 150 and 156 are inadvertently oriented horizontally. The containment tube 172 that is in fluid communication with the high pressure area 197, and a containment area 266 (illustrated in FIGS. 2c and 4a) that is in fluid communication with the reduced-pressure exhaust area 192, may be designed and arranged to further contain lubricant and reduce spillage. In addition, check valves, flappers, pilot control valves, float valves, and other fluid control devices are contemplated to reduce or prevent lubricant spillage.

Although only a few exemplary embodiments of this invention have been described in detail above, those skilled in the art will readily appreciate that many modifications are possible in the exemplary embodiments without materially departing from the novel teachings and advantages of this invention. Also, features illustrated and discussed above with respect to some embodiments can be combined with features illustrated and discussed above with respect to other embodiments. Accordingly, all such modifications are intended to be included within the scope of this invention.

What is claimed is:

1. A lubrication cartridge for a surgical instrument, comprising:
   a lubricant reservoir configured to house a lubricating material;
   a pressurized fluid inlet configured to be coupled to a first passage and allow inflow of a pressurized fluid into the lubricant reservoir;
   a lubricant outlet configured to be coupled to a second passage and allow outflow of the pressurized fluid from the lubricant reservoir; and a metering insert located between the lubricant outlet and the second passage;

wherein the metering insert defines at least one path through the metering insert that controls a flow of lubricant between the lubricant reservoir and the second passage.

2. The lubrication cartridge for a surgical instrument of claim 1, wherein the at least one path of the metering insert includes a plurality of paths.

3. The lubrication cartridge for a surgical instrument of claim 2, wherein each path of the plurality of paths interconnects the lubricant outlet and the second passage.

4. The lubrication cartridge for a surgical instrument of claim 3, wherein the metering material is formed of a porous metal and each path of the plurality of paths is formed in the porous metal.

5. The lubrication cartridge for a surgical instrument of claim 3, wherein the metering material is formed of a sintered metal and each path of the plurality of paths is formed in the sintered metal.

6. The lubrication cartridge for a surgical instrument of claim 2, wherein the plurality of paths are formed by the metering insert is a random arrangement of paths.

7. The lubrication cartridge for a surgical instrument of claim 2, wherein the metering insert is shaped to achieve a flow rate through the metering insert.

8. The lubrication cartridge for a surgical instrument of claim 7, wherein the metering insert is shaped as at least one of a solid cylinder, a hollow cylinder, a disc, or a half sphere.

9. The lubrication cartridge for a surgical instrument of claim 1, further comprising:
a cartridge body, wherein the lubricant reservoir is defined within the cartridge body; and
a cartridge coupling located on the cartridge body and defining the first passage and the second passage.

10. The lubrication cartridge for a surgical instrument of claim 1, further comprising:
a startup lubrication mechanism operable to release an initial non-metered quantity of lubricant into one of the first and second passages for initial lubrication of the surgical instrument that is coupled to the lubrication cartridge, wherein the metering insert is configured to allow a subsequent metered quantity of lubricant into the second passage for continued lubrication of the surgical instrument after the release of the initial non-metered quantity of lubricant.

11. The lubrication cartridge for a surgical instrument of claim 1, wherein the metering insert is disposable and the lubrication cartridge is reusable wherein the metering insert is user-replaceable relative to the lubrication cartridge.

12. A lubrication cartridge for a surgical instrument and a stem configured to be coupled to the surgical instrument, comprising:
a lubrication cartridge separate and mateable to the stem;
a first coupling interface located on the lubrication cartridge configured to be coupled to a second coupling interface located on the stem, wherein the first coupling interface and the second coupling interface are configured to sealing mate the lubrication cartridge with the stem;
a lubricant reservoir defined at least in part by the lubrication cartridge; and a metering insert located between the lubricant reservoir and a primary fluid path and operable to meter lubricant flow from the lubricant reservoir to the primary flow path;
wherein the lubrication cartridge is configured to be moveable relative to the stem from an initial coupling orientation to a final coupling orientation.

13. The lubrication cartridge for a surgical instrument of claim 12, wherein in the initial coupling configuration the first coupling interface located on the lubrication cartridge contacts the second coupling interface located on the stem in a first orientation and in the final coupling orientation the first coupling interface located on the lubrication cartridge contacts the second coupling interface located on the stem in a second orientation different from the first orientation.

14. The lubrication cartridge for a surgical instrument of claim 12, further comprising:
a securing tab extending from the lubrication cartridge configured to engage a stem detent formed in the stem at least when the lubrication cartridge and the stem are in the final coupling orientation.

15. The lubrication cartridge for a surgical instrument of claim 14, wherein the securing tab is configured to be frangible to break away from the lubrication cartridge when moving the lubrication cartridge from the final coupling orientation after the lubrication cartridge has been moved into the final coupling orientation.

16. The lubrication cartridge for a surgical instrument of claim 14, wherein the securing tab is configured to be functionally inoperable upon moving the lubrication cartridge from the final coupling orientation after the lubrication cartridge has been moved into the final coupling orientation such that the lubrication cartridge becomes unusable when the securing tab is functionally inoperable.

17. The lubrication cartridge for a surgical instrument of claim 12, further comprising:
a coupling support recess formed by the lubrication cartridge configured to engage a stem coupling support projection extending from the stem when the lubrication cartridge and the stem are in the final coupling orientation.

18. The lubrication cartridge for a surgical instrument of claim 12, wherein the lubrication cartridge has an exterior surface that defines a recess that at least partially surrounds the stem when the lubrication cartridge and the stem are in the final coupling orientation.

19. The lubrication cartridge for a surgical instrument of claim 12, further comprising:
a seal formed on the lubrication cartridge configured to be pierced by a piercing portion associated with the stem when the lubrication cartridge and the stem are in the final coupling orientation.

20. The lubrication cartridge for a surgical instrument of claim 19, further comprising:
a startup lubrication system formed within the lubrication cartridge operable to release a quantity of lubricant that by-passes the metering insert when the piercing portion initially pierces the seal.

21. The lubrication cartridge for a surgical instrument of claim 12, wherein the lubrication cartridge is rotated approximately 90 degrees relative to the stem between the initial coupling orientation and the final coupling orientation.

22. A lubrication cartridge for a surgical instrument, comprising:
a lubrication cartridge separate and mateable to a stem wherein the lubrication cartridge has an exterior wall that defines a curved configuration to mate with the stem;
a lubricant reservoir defined at least in part by the lubrication cartridge;

an exhaust portion defined at least in part by the lubrication cartridge, wherein an exhaust fluid returning from the surgical instrument passes through the exhaust portion; and a first coupling interface located on the lubrication cartridge wherein the first coupling interface is configured to sealing mate the lubrication cartridge with the stem; and wherein the lubrication cartridge and the stem comprise an initial coupling orientation and a final coupling orientation.

23. The lubrication cartridge for a surgical instrument of claim 22, further comprising:

a stem configured to be coupled to the surgical instrument, wherein the stem includes:
 a central body member defining a primary passage; and
 a kick guard extending from the central body member and complimentary in shape to at least a portion of the lubrication cartridge.

24. The lubrication cartridge for a surgical instrument of claim 23, wherein the stem further comprises a second coupling interface;

wherein the first coupling interface engages the second coupling interface located on the stem.

25. The lubrication cartridge for a surgical instrument of claim 24, wherein the stem coupling defines a first opening having a first cross-sectional area for passage of a fluid from the lubrication cartridge and a second openings having a second cross-sectional area that is larger than the first cross-section area for passing exhaust fluid from the surgical instrument to the exhaust portion.

26. The lubrication cartridge for a surgical instrument of claim 22, wherein the exhaust portion further comprises:

at least one baffle wall to alter the direction of the exhaust flow of the fluid from the surgical instrument; and a filter configured to capture at least a portion of the lubrication in the exhaust fluid.

27. The lubrication cartridge for a surgical instrument of claim 22, wherein the lubrication cartridge includes a first passage for initial unmetered lubrication flow and a second passage for metered lubrication flow.

* * * * *

UNITED STATES PATENT AND TRADEMARK OFFICE
CERTIFICATE OF CORRECTION

PATENT NO.        : 8,459,414 B2
APPLICATION NO.   : 13/647157
DATED             : June 11, 2013
INVENTOR(S)       : S. Shane Dexter et al.

Page 1 of 1

It is certified that error appears in the above-identified patent and that said Letters Patent is hereby corrected as shown below:

In the Claims

Column 20, line 6, claim 25, "and a second openings having" should be -- and a second opening having --.

Signed and Sealed this
Third Day of December, 2013

Margaret A. Focarino
*Commissioner for Patents of the United States Patent and Trademark Office*